(12) United States Patent
Taylor et al.

(10) Patent No.: US 11,686,415 B2
(45) Date of Patent: Jun. 27, 2023

(54) COMPACT PORTABLE OXYGEN CONCENTRATOR

(71) Applicant: Inogen, Inc., Goleta, CA (US)

(72) Inventors: Brenton Alan Taylor, Kenwood, CA (US); Peter James Hansen, Santa Barbara, CA (US); Daniel Wayne Chin, Summerland, CA (US); Patrick Fitzlindon Burgess, Dunedin, FL (US); Michael Pollack, Goleta, CA (US)

(73) Assignee: Inogen, Inc., Goleta, CA (US)

( * ) Notice: Subject to any disclaimer, the term of this patent is extended or adjusted under 35 U.S.C. 154(b) by 343 days.

(21) Appl. No.: 16/837,816

(22) Filed: Apr. 1, 2020

(65) Prior Publication Data
US 2020/0306485 A1 Oct. 1, 2020

Related U.S. Application Data

(60) Provisional application No. 62/827,689, filed on Apr. 1, 2019.

(51) Int. Cl.
*B01D 53/047* (2006.01)
*A61M 16/00* (2006.01)
(Continued)

(52) U.S. Cl.
CPC ......... *F16L 39/04* (2013.01); *A61M 16/0063* (2014.02); *A61M 16/0875* (2013.01);
(Continued)

(58) Field of Classification Search
CPC ............... F16L 39/04; A61M 16/0063; A61M 16/0875; A61M 16/101; A61M 2016/1025; A61M 2202/0208; A61M 2205/3331; A61M 2205/3375; A61M 2205/3606; A61M 2205/362; A61M 2205/8206; A61M 2230/42; B01D 53/0407; B01D 53/053;
(Continued)

(56) References Cited

U.S. PATENT DOCUMENTS

| 3,460,532 A | 8/1969 | Bird |
| 4,342,573 A | 8/1982 | McCombs |

(Continued)

FOREIGN PATENT DOCUMENTS

| EP | 1289032 A1 | 5/2003 |
| EP | 2392375 A2 | 12/2011 |

(Continued)

*Primary Examiner* — Frank M Lawrence, Jr.
(74) *Attorney, Agent, or Firm* — Knobbe Martens Olson & Bear, LLP

(57) ABSTRACT

A battery retaining system for a portable oxygen concentrator includes a first rail configured to receive a first slide of a battery, a second rail configured to receive a second slide of the battery, the second rail being spaced apart from the first rail so as to form a channel configured to receive the battery, and a flexible stiffening mechanism configured to impart a biasing force on a surface of the battery when the battery is received within the channel. The flexible stiffening mechanism includes a protrusion projecting from the first rail at least partially towards the second rail and a slit positioned behind the protrusion and configured to facilitate travel of the protrusion fore and aft.

20 Claims, 26 Drawing Sheets

(51) Int. Cl.
*F16L 39/04* (2006.01)
*A61M 16/10* (2006.01)
*A61M 16/08* (2006.01)
*F04B 53/16* (2006.01)
*G01N 33/00* (2006.01)
*G01N 33/497* (2006.01)
*F04B 49/06* (2006.01)
*F04C 28/08* (2006.01)
*F04D 27/00* (2006.01)
*H03K 3/017* (2006.01)
*B01D 53/04* (2006.01)
*B01D 53/053* (2006.01)
*H01M 50/247* (2021.01)
*H01M 50/284* (2021.01)
*H01M 50/204* (2021.01)
*B01D 53/00* (2006.01)

(52) U.S. Cl.
CPC ....... *A61M 16/101* (2014.02); *B01D 53/0407* (2013.01); *B01D 53/053* (2013.01); *F04B 49/06* (2013.01); *F04B 53/16* (2013.01); *F04C 28/08* (2013.01); *F04D 27/004* (2013.01); *G01N 33/0031* (2013.01); *G01N 33/497* (2013.01); *H01M 50/204* (2021.01); *H01M 50/247* (2021.01); *H01M 50/284* (2021.01); *H03K 3/017* (2013.01); *A61M 2016/1025* (2013.01); *A61M 2202/0208* (2013.01); *A61M 2205/3331* (2013.01); *A61M 2205/3375* (2013.01); *A61M 2205/362* (2013.01); *A61M 2205/3606* (2013.01); *A61M 2205/8206* (2013.01); *A61M 2230/42* (2013.01); *B01D 53/00* (2013.01); *B01D 2256/12* (2013.01); *B01D 2257/102* (2013.01); *B01D 2257/40* (2013.01); *B01D 2259/4533* (2013.01); *B01D 2259/4541* (2013.01); *F05B 2270/301* (2013.01)

(58) Field of Classification Search
CPC .... B01D 53/00; B01D 53/04; B01D 2256/12; B01D 2257/102; B01D 2257/40; B01D 2259/4533; B01D 2259/4541; B01D 53/047; B01D 53/0415; B01D 53/06; F04B 49/06; F04B 53/16; F04C 28/08; F04D 27/004; G01N 33/0031; G01N 33/497; H03K 3/017; F05B 2270/301; H01M 50/247; H01M 50/284; H01M 50/204; Y02E 60/10
USPC ......................................... 95/130; 128/205.27
See application file for complete search history.

(56) References Cited

U.S. PATENT DOCUMENTS

| | | | |
|---|---|---|---|
| 4,371,384 A | 2/1983 | McCombs | |
| 4,378,982 A * | 4/1983 | McCombs | B01D 53/0407 96/117 |
| 5,601,786 A * | 2/1997 | Monagan | A61L 9/20 422/123 |
| 6,729,415 B1 | 5/2004 | Huang | |
| 6,840,335 B1 | 1/2005 | Wu | |
| 7,329,304 B2 | 2/2008 | Bliss | |
| 7,438,745 B2 | 10/2008 | Deane | |
| 7,575,624 B2 | 8/2009 | Cartwright | |
| 7,730,887 B2 | 6/2010 | Deane | |
| 7,753,996 B1 | 7/2010 | Deane | |
| 7,837,761 B2 | 11/2010 | Bliss | |
| 8,187,367 B2 * | 5/2012 | Wang | B01D 53/047 96/380 |
| 8,440,004 B2 * | 5/2013 | Taylor | A61M 16/101 96/121 |
| 9,316,216 B1 | 4/2016 | Cook | |
| 10,799,663 B1 | 10/2020 | Oddo | |
| 11,135,392 B2 | 10/2021 | Oddo | |
| 2002/0062681 A1 | 5/2002 | Livingston | |
| 2004/0081883 A1 | 4/2004 | Mooty | |
| 2005/0045040 A1 | 3/2005 | McCombs | |
| 2005/0072423 A1 | 4/2005 | Deane | |
| 2005/0103341 A1 * | 5/2005 | Deane | A61M 16/101 128/204.26 |
| 2007/0137487 A1 * | 6/2007 | Whitley | B01D 53/0415 96/121 |
| 2007/0277824 A1 | 12/2007 | Aylsworth | |
| 2008/0087170 A1 | 4/2008 | Deane | |
| 2008/0105258 A1 | 5/2008 | Deane | |
| 2009/0236849 A1 | 9/2009 | Takasaki | |
| 2009/0246608 A1 | 10/2009 | Wu | |
| 2010/0099002 A1 | 4/2010 | Andreas-Schott | |
| 2010/0192775 A1 * | 8/2010 | Wang | B01D 53/047 96/116 |
| 2012/0055477 A1 * | 3/2012 | Wilkinson | A61M 16/101 128/204.23 |
| 2012/0167888 A1 | 7/2012 | Taylor | |
| 2013/0074964 A1 | 3/2013 | Wu | |
| 2014/0110892 A1 | 4/2014 | Wojcieson | |
| 2014/0190348 A1 * | 7/2014 | Richey, II | B01D 53/0423 96/116 |
| 2014/0216461 A1 | 8/2014 | Koeppel | |
| 2014/0224246 A1 | 8/2014 | Whitcher | |
| 2014/0345609 A1 | 11/2014 | Whitcher | |
| 2014/0360891 A1 | 12/2014 | Kline | |
| 2015/0059741 A1 | 3/2015 | Ota | |
| 2015/0136126 A1 | 5/2015 | Sims | |
| 2015/0140384 A1 | 5/2015 | Chellew | |
| 2015/0182720 A1 * | 7/2015 | Taylor | B01D 53/0438 128/205.12 |
| 2015/0209544 A1 | 7/2015 | Morita | |
| 2015/0231551 A1 | 8/2015 | Wilkinson | |
| 2016/0032943 A1 | 2/2016 | Eddie | |
| 2016/0375218 A1 | 12/2016 | Sprinkle | |
| 2017/0021302 A1 | 1/2017 | Galbraith | |
| 2017/0059074 A1 | 3/2017 | Wu | |
| 2017/0196376 A1 | 7/2017 | Leonard | |
| 2017/0276421 A1 | 9/2017 | Candeo | |
| 2018/0112908 A1 | 4/2018 | Song | |
| 2018/0291885 A1 | 10/2018 | Grybush | |
| 2019/0093648 A1 | 3/2019 | Ventrapragada | |
| 2019/0120255 A1 | 4/2019 | Tomeo | |
| 2019/0126188 A1 | 5/2019 | Dolensky | |
| 2019/0126189 A1 | 5/2019 | Dolensky | |
| 2019/0175856 A1 | 6/2019 | Galbraith | |
| 2019/0217042 A1 | 7/2019 | Zapol | |
| 2020/0040912 A1 | 2/2020 | Nanjappa | |
| 2021/0113801 A1 | 4/2021 | Wang | |

FOREIGN PATENT DOCUMENTS

| | | |
|---|---|---|
| WO | WO 2015/116788 A1 | 8/2015 |
| WO | WO 2017/007802 A1 | 1/2017 |
| WO | WO 2020/001872 A1 | 1/2020 |

* cited by examiner

181

182
181

183
181
183

183
181
183
182

COMPACT PORTABLE OXYGEN CONCENTRATOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims priority benefit of U.S. Provisional Application No. 62/827,689, entitled "COMPACT PORTABLE OXYGEN CONCENTRATOR," filed Apr. 1, 2019, which is incorporated herein by reference in its entirety.

BACKGROUND

Field

The present disclosure relates to oxygen concentrators for personal use and in particular to portable oxygen concentrators.

Description of the Related Art

Personal oxygen concentrators are devices that convert ambient air to an oxygen enriched gas for therapeutic use. They are becoming increasingly popular as alternatives to liquid oxygen vessels and compressed gas cylinders. Such personal oxygen concentrators exist in both portable form for ambulatory use and stationary form for use inside the home. To be practical for everyday use by patients needing therapeutic oxygen, portable oxygen concentrators are generally preferred over stationary ones. It is desirable that such portable oxygen concentrators be small, lightweight, efficient, reliable, and relatively inexpensive. Efforts to design an oxygen concentrator having all of these desirable attributes may be inherently limited by the size and weight of the individual components. Further reductions in size and weight of portable oxygen concentrators without sacrificing performance may require new approaches to concentrator design.

SUMMARY

Portable oxygen concentrator elements may be provided that include improved compressor control features, high density gas tight interconnects, integrated sensor blocks, space efficient adsorber designs, improved airflow, and improved battery retention. The result of the elements is an extremely compact, light reliable portable oxygen concentrator that is easy to assemble and relatively inexpensive.

In one aspect, a battery retaining system for a portable oxygen concentrator is provided. The battery retaining system includes a first rail configured to receive a first slide of a battery, a second rail configured to receive a second slide of the battery, the second rail being spaced apart from the first rail so as to form a channel configured to receive the battery, and a flexible stiffening mechanism configured to impart a biasing force on a surface of the battery when the battery is received within the channel. The flexible stiffening mechanism includes a protrusion projecting from the first rail at least partially towards the second rail and a slit positioned behind the protrusion and configured to facilitate travel of the protrusion fore and aft.

In some embodiments, the system further includes one or more protrusions projecting from the second rail at least partially towards the first rail, the one or more protrusions being configured to contact the battery when the battery is positioned within the channel. In some embodiments, the channel extends between an open proximal end and a closed distal end, wherein at least one of the one or more protrusions projecting from the second rail are positioned proximally relative to the protrusion of the first rail. In some embodiments, the channel extends between an open proximal end and a closed distal end, wherein at least one of the one or more protrusions projecting from the second rail are positioned distally relative to the protrusion of the first rail. In some embodiments, the one or more protrusions projecting from the second rail comprise a first protrusion positioned proximally relative to the protrusion of the first rail and a second protrusion positioned distally relative to the protrusion of the first rail. In some embodiments, the flexible stiffening mechanism maintains contact between the first rail and the battery to stabilize the battery within the channel, the battery having a battery size that is smaller than an upper tolerance level. In some embodiments, the flexible stiffening is configured to impart the biasing force on the surface of the battery so as to align an electrical connector of the battery with an electrical connector of the portable oxygen concentrator. In some embodiments, the flexible stiffening mechanism is configured to impart the biasing force on the surface of the battery to impart stability to the installation of the battery. In some embodiments, the biasing force of the flexible stiffening mechanism is sufficiently flexible to permit translation of the battery within the channel past the protrusion.

In another aspect, a portable oxygen concentrator is provided. The portable oxygen concentrator includes a chassis base, a printed circuit board mounted at a superior end of the chassis base, the printed circuit board including a first electrical connector, and an outer housing configured to removably couple to the chassis base. The outer housing includes one or more controls of a user interface and a second electrical connector in electrical communication with the controls of the user interface, the second electrical connector being positioned to align with and mate with the first electrical connector when the outer housing is coupled to the chassis base.

In some embodiments, the printed circuit board comprises a user interface display. In some embodiments, the outer housing is configured to define an enclosed volume around the printed circuit board when coupled to the chassis base. In some embodiments, the outer housing is configured to seal the enclosed printed circuit board from external moisture when coupled to the chassis base. In some embodiments, the first electrical connector is oriented on the printed circuit board so as to face in a generally superior direction and the second electrical connector is oriented on the outer housing so as to face in a generally inferior direction.

In another aspect, a gas concentrator is provided. The gas concentrator includes a chassis base, a compressor assembly, an outer housing coupled to the chassis base so as to define an internal volume enclosing the compressor assembly, and a shell structure positioned within the internal volume, the shell structure including one or more insulating panels disposed about the compressor assembly.

In some embodiments, the shell structure separates the compressor assembly from one or more elements positioned within the internal volume of the concentrator, the one or more elements comprising one or more adsorbers coupled to the chassis base, one or more pneumatic modules, one or more electronic modules, or one or more sensor modules. In some embodiments, the shell structure forms at least a portion of an at least partially sealed chamber around the compressor assembly. In some embodiments, the gas concentrator further includes a printed circuit board, the printed circuit board forming at least a portion of the at least partially sealed chamber. In some embodiments, an interior surface of the outer housing forms at least a portion of the at least partially sealed chamber.

In another aspect, a gas concentrator is provided. The gas concentrator includes a chassis base, a compressor assembly, an airflow generator, one or more exhaust ports, and an outer housing coupled to the chassis base so as to define an internal volume enclosing the compressor assembly and the airflow generator, the outer housing including one or more air inlets, wherein the one or more air inlets are recessed within the outer housing or extend along a curved or angled surface of the outer housing, wherein the airflow generator is configured to direct airflow along an airflow path between the one or more air inlets and the one or more exhaust ports.

In some embodiments, the one or more air inlets include a first air inlet and a second air inlet, wherein the first air inlet and the second air inlet are positioned on opposite surfaces of the housing. In some embodiments, the one or more exhaust ports comprise a first exhaust port and a second exhaust port, wherein the first exhaust port and the second exhaust port are formed within opposite side surfaces of the chassis base. In some embodiments, the gas concentrator further includes a battery coupled to the chassis base, wherein the one or more exhaust ports are formed in a portion of the chassis base extending laterally beyond a lateral edge of the battery. In some embodiments, the exhaust ports are directed at a downward angle over a recess formed in the portion of the chassis base extending laterally beyond a lateral edge of the battery, thereby preventing obstruction of the exhaust ports if the concentrator is placed adjacent a flat surface.

In another aspect, an adsorber for a gas concentrator is provided. The adsorber includes an adsorbent material including adsorbent particles and a vessel housing the adsorbent material. The vessel includes a vessel wall having a non-circular cross section and at least one stiffening support, wherein a combination of a thickness of the vessel wall and a stiffness of the stiffening support is sufficient to limit deformation of the vessel wall to at least one of less than 0.1 mm and less than 25% of an average diameter of the adsorbent particles under a pressure swing of at least 30 psi within the vessel.

In some embodiments, the deformation of the vessel wall is less than 0.05 mm under a pressure swing of at least 30 psi within the vessel. In some embodiments, a cross section of the adsorber is at least 90% filled with the adsorbent material. In some embodiments, the vessel wall has an oblong cross section. In some embodiments, the at least one stiffening support includes a stiffening rib extending at least one of across an interior of the vessel and along an interior wall of the vessel. In some embodiments, the at least one stiffening support includes a stiffening rib positioned on an exterior surface of the vessel. In some embodiments, the adsorber further includes a filter positioned within a cavity formed by a protrusion extending from a superior end of the vessel, the protrusion having a cross section different than the cross section of the vessel wall. In some embodiments, the protrusion is cylindrical. In some embodiments, the protrusion is integrally formed with the vessel wall.

In another aspect, an adsorber for a gas concentrator is provided. The adsorber includes an adsorbent material including adsorbent particles and a vessel housing the adsorbent material. The vessel includes a vessel wall having a non-circular cross section and at least one stiffening support, wherein a cross section of the adsorber is at least 90% filled with the adsorbent material.

In some embodiments, the vessel wall has an oblong cross section. In some embodiments, the at least one stiffening support including a stiffening rib extending at least one of across an interior of the vessel and along an interior wall of the vessel. In some embodiments, the at least one stiffening support includes a stiffening rib positioned on an exterior surface of the vessel. In some embodiments, the adsorber further includes a filter positioned within a cavity formed by a protrusion extending from a superior end of the vessel, the protrusion having a cross section different than the cross section of the vessel wall. In some embodiments, the protrusion is cylindrical. In some embodiments, the protrusion is integrally formed with the vessel wall.

In another aspect, an adsorber system is provided. The adsorber system includes a first adsorber including an adsorbent material including adsorbent particles and a vessel housing the adsorbent material. The vessel includes a vessel wall having a non-circular cross section and at least one stiffening support. The adsorber system includes a second adsorber including an adsorbent material comprising adsorbent particles and a vessel housing the adsorbent material. The vessel includes a vessel wall having a non-circular cross section and at least one stiffening support. The vessel wall of the first adsorber is joined to the vessel wall of the second adsorber.

In some embodiments, the vessel wall of the first adsorber is integrally formed with the vessel wall of the second adsorber. In some embodiments, the stiffening support of the first adsorber is aligned with the stiffening support of the second adsorber. In some embodiments, the vessel wall of the first adsorber and the vessel wall of the second adsorber each comprise an oblong cross section.

In another aspect, a compressor assembly for a portable oxygen concentrator is provided. The compressor assembly includes a first compressor chamber including a first connector, a second compressor chamber including a connector, and a tube including a first end including a first connection interface configured to connect to the first connector and a second end including a second connection interface configured to connect to the second connector, wherein the first connection interface is shaped to maintain the connection between the first connector and the first connection interface in a fixed orientation and the second connection interface is shaped to maintain the connection between the second connector and the second connection interface in a fixed orientation, wherein one or more of the first connector, the second connector, and the tube are compliant.

In some embodiments, the first connector has a shape and the first connection interface of the tube has a shape that matches the shape of the first connector. In some embodiments, the second connector has a shape and the second connection interface has a shape that matches the shape of the second connector. In some embodiments, the shapes of the first connection interface, the second connection interface, the first connector, and the second connector are square.

In another aspect, a compressor assembly for a portable oxygen concentrator is provided. The compressor assembly includes a compliant mount including at least one connector. The at least one connector includes a compliant member and a pair of protruding tabs extending from the compliant member. The compressor assembly further includes a compressor including a first compressor chamber, a second compressor chamber, and at least one pair of slots, the at least one pair of slots configured to receive the pair of protruding tabs of the at least one connector.

In some embodiments, the protruding tabs are spaced 180° apart from one another around a circumference of the compliant member. In some embodiments, the pair of protruding tabs are formed of a different material than the compliant member. In some embodiments, the compliant mount is coupled to the compressor by a hollow screw. In some embodiments, intake air is drawn through the hollow screw. In some embodiments, the at least one connector comprises two connectors.

In another aspect, a sensor assembly is provided. The sensor assembly includes an oxygen sensor, the oxygen sensor including at least one emitter including an active surface configured to emit an acoustic signal, at least one receiver including an active surface configured to receive the acoustic signal, and a body forming a chamber. The body includes a first opening configured to receive the at least one emitter such that the active surface of the at least one emitter is exposed to the chamber, a second opening configured to receive the at least one receiver such that the active surface of the at least one receiver is exposed to the chamber, and at least two reflectors configured to reflect the acoustic signal so as to establish an acoustic path between the active surface of the emitter and the active surface of the receiver.

In some embodiments, the first opening and the second opening are coplanar. In some embodiments, the active surface of the emitter and the active surface of the receiver are coplanar. In some embodiments, the active surface of the emitter and the active surface of the receiver are oriented to face in parallel directions. In some embodiments, the oxygen sensor further includes one or more sealing rings configured to provide a seal between the first opening and the emitter and the second opening and the receiver. In some embodiments, the sensor assembly further includes a printed circuit board, wherein the emitter and receiver are mounted to the printed circuit board, and wherein the printed circuit board is mounted to the body. In some embodiments, the oxygen sensor includes a temperature sensor configured to measure a temperature of oxygen gas within the chamber. In some embodiments, the oxygen sensor includes a temperature sensor configured to measure a temperature of air outside the chamber. In some embodiments, the oxygen sensor includes a pressure sensor configured to measure a pressure of oxygen gas within the chamber. In some embodiments, the oxygen sensor includes a pressure sensor configured to measure a pressure of air outside the chamber. In some embodiments, the sensor assembly further includes a breath detection sensor.

In another aspect, a method of operating a compressor system is provided. The method includes determining an efficiency of a compressor configured to operate at a plurality of output flow settings. The compressor system includes a motor, a power source providing a DC power source voltage, a voltage controller configured to selectively modify the power source voltage to provide a plurality of supply voltages, and a pulse width modulation controller configured to selectively apply pulse width modulation to the supply voltages at a plurality of pulse width modulation duty cycles, thereby providing a plurality of motor control signals. Determining an efficiency of the compressor includes one or more of measuring, calibrating, calculating, or modeling motor efficiency over a range of supply voltage and pulse width modulation duty cycle combinations, each combination comprising a supply voltage of the plurality of supply voltages and a pulse width modulation duty cycle of the plurality of pulse width modulation duty cycles. The method further includes selecting a supply voltage of the plurality of supply voltages and a pulse width modulation duty cycle of the plurality of pulse width modulation duty cycles for use at at least one output flow setting of the plurality of output flow settings based on the determined efficiency of the compressor, generating the selected supply voltage by maintaining, reducing, or increasing a nominal supply voltage, and applying the selected pulse width modulation duty cycle.

In some embodiments, the nominal supply voltage is a desired supply voltage for one of the plurality of output flow settings. In some embodiments, the nominal supply voltage is a desired supply voltage for a maximum output flow setting of the plurality of output flow settings. In some embodiments, the power source is one of a battery, a fixed power source comprising car DC power ports, or an AC to DC power supply. In some embodiments, the power source is a battery, and the method further includes dynamically monitoring the power source voltage and adjusting one or both of the supply voltage and the pulse width modulation duty cycle to accommodate power source voltage changes to achieve a desired efficiency of the compressor. In some embodiments, the compressor system is part of a swing adsorption system and the method further include monitoring a pressure profile over the course of a pressure swing adsorption cycle, a pressure-vacuum swing adsorption cycle, or a vacuum swing adsorption cycle and dynamically adjusting the supply voltage and pulse width modulation duty cycle to improve efficiency over the course of the pressure swing adsorption cycle, the pressure-vacuum swing adsorption cycle, or the vacuum swing adsorption cycle. In some embodiments, monitoring the head profile and adjusting the supply voltage and pulse width modulation duty cycle are performed during the pressure swing adsorption cycle, the pressure-vacuum swing adsorption cycle, or the vacuum swing adsorption cycle. In some embodiments, monitoring the head profile includes monitoring one or more of current measurements, power measurements, and pressure measurements through a feed forward process. In some embodiments, the nominal supply voltage is used without pulse width modulation as the motor control signal for a highest output flow setting of the plurality of outflow settings of the compressor. In some embodiments, a combination of supply voltage regulation and pulse width modulation are applied to the nominal supply voltage to provide motor control signals for one or more output flow settings lower than the highest output flow setting of the compressor. In some embodiments, the selected supply voltage and the selected pulse width modulation duty cycle are selected to optimize efficiency at a most commonly used output flow setting of the plurality of output flow settings while maintaining the ability to operate at each of the plurality of output flow settings. In some embodiments, the selected supply voltage and the selected pulse width modulation duty cycle are selected to reduce switching losses at at least one output flow setting of the plurality of output flow settings. In some embodiments, the voltage controller is configured to modify the power source voltage to provide one or more supply voltages higher than the power source voltage.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced ele

DETAILED DESCRIPTION

Personal use therapeutic oxygen concentrators that convert ambient air into oxygen enriched gas are increasing in popularity, both in portable and stationary forms. They are generally much smaller in size and different in design as compared to industrial gas concentrators. An example portable oxygen concentrator, including its use and operation, is described in co-pending U.S. application Ser. No. 15/427,948, entitled "GAS CONCENTRATOR WITH REMOVABLE CARTRIDGE ADSORBENT BEDS," which is incorporated herein by reference in its entirety. Another example of such a portable oxygen concentrator is described in U.S. application Ser. No. 15/608,775, entitled "COMPACT PORTABLE OXYGEN CONCENTRATOR," which is incorporated by reference in its entirety. Another example of such a portable oxygen concentrator is described in U.S. application Ser. No. 15/608,788, entitled "GAS CONCENTRATOR WITH REMOVABLE CARTRIDGE ADSORBENT BEDS," which is incorporated herein by reference in its entirety. Such oxygen concentrators, because of their small size and intended personal use, have differing design considerations from large industrial concentrators intended to produce large quantities of concentrated gas. For example, in an illustrative embodiment, the portable concentrator according to the present disclosure may be between 25 and 200 cubic inches in size, between 2 and 7 pounds in weight, and may produce between 300 and 3000 ml/min of concentrated oxygen.

Figure 1A:
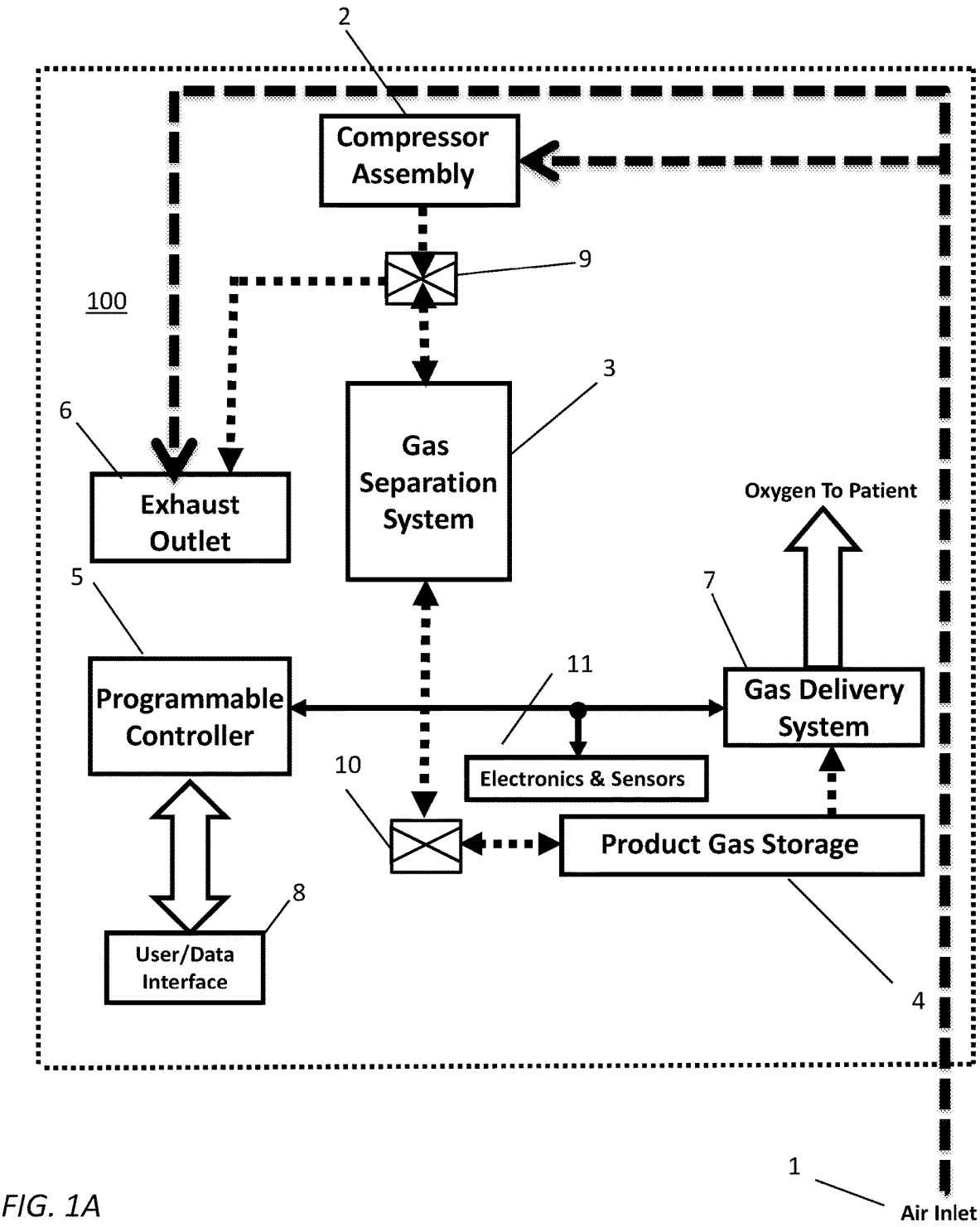
- FIG. 1A shows a simplified system block diagram of an exemplary portable oxygen concentrator.

FIG. 1A is a schematic illustration of an exemplary oxygen concentrator system 100 in accordance with an embodiment of the present disclosure. As shown in FIG. 1A, the system 100 generally includes an air inlet 1 through which ambient air is drawn into the system, a compressor assembly 2 for pressurizing the ambient air to provide a feed gas, a gas separation unit or system 3 which receives and processes the feed gas to produce a product gas having a higher oxygen content than the ambient air, a gas delivery system 7, such as a conserver, for delivering the oxygen-rich product gas to a patient, and an exhaust outlet or port 6 for releasing nitrogen-rich waste gas and spent cooling airflow gas. As used herein, spent cooling airflow gas can refer to airflow gas that has been used to cool portions of the concentrator system 100. The system 100 further includes a feed/waste manifold 9, a product valve manifold 10, a product gas storage 4, a user/data interface 8, and a programmable controller 5 for controlling the operation of the system.

In some embodiments, ambient air drawn into the system through air inlet 1 can be used to supply the gas separation system 3 with pressurized gas to flush out nitrogen-rich waste gas. Ambient air drawn into the system through the air inlet 1 can also be used to cool the internal components of the system. This air movement may be provided by an airflow generator, such as a fan or blower, located at the air inlet 1, at the exhaust outlet 6, or along an air flow path between the air inlet 1 and the exhaust outlet 6. To achieve proper air flow, an airflow generator may be employed in some embodiments. In some embodiments, airflow may be generated, for example, by a cooling fan or blower. In some embodiments, the cooling fan or blower can have dimensions in the range of 40 mm×40 mm to 100 mm×100 mm in diameter and 20 mm to 60 mm in depth. One or more fans in varying sizes and locations may also be employed in some embodiments to optimize air flow and minimize noise. As indicated schematically in FIG. 1A, the air flow may be directed to pass over the internal components of the oxygen concentrator system 100. In some embodiments, the waste gas from the gas separation system 3 and the spent cooling gas both exit the system 100 via the exhaust outlet 6. In some embodiments, the exhaust outlet 6 is positioned adjacent or immediately adjacent the compressor assembly 2. In some embodiments, the air flow path directs cool air to pass over the other components of the system before reaching the compressor assembly 2. The compressor assembly 2 can generate significant heat during operation. In some embodiments, the compressor assembly 2 is placed adjacent to the exhaust outlet 6 to achieve improved cooling effectiveness. In some embodiments, an airflow generator, such as a fan, blower, or other means, may be positioned along the air flow path to push and/or pull air through the system 100 interior from the air inlet 1 to the exhaust outlet 6 or between the air inlet 1 and the exhaust outlet 6. In some embodiments, a plurality of air inlets and/or a plurality of exhaust outlets may be employed to achieve appropriate cooling. In some embodiments, the concentrator 100 can include a plurality of airflow generators to achieve appropriate cooling.

In some embodiments, the gas separation system 3 is a pressure swing adsorption (PSA) gas separation system. In some embodiments, the gas separation system 3 is a vacuum swing adsorption (VSA) system. In some embodiments, the gas separation system 3 is a vacuum pressure swing adsorption (VPSA) system. The gas separation system 3 may include one or more adsorbers. The adsorbers can employ pressure, vacuum, or a combination thereof to separate the components of ambient air to produce an oxygen-rich product gas. Ambient air is drawn in by the compressor assembly 2 through a filter and through an elongated and/or tortuous air path designed to minimize the escape of noise caused by the compressor assembly 2. In some embodiments, the compressor assembly 2 may include a single cylinder or multi-cylinder reciprocating piston compressor employing pressure or a combination of pressure and vacuum cylinders. In some embodiments, the compressor assembly 2 may alternatively or additionally include other compressors types such as scroll, linear free piston, rotary vane, rotary screw, conical screw, or diaphragm type compressors.

Pressurized air may be discharged from the compressor assembly 2 at a rate of 5 SLPM to 15 SLPM per LPM or approximately 5 SLPM to 15 SLPM per LPM of oxygen-rich gas produced at a pressure up to 3 bar. The pressurized air is directed to one of two or more adsorbers of the gas separation system 3 by one or more feed/waste valves that may be housed in a feed/waste manifold 9. The feed/waste valve configuration in the feed/waste manifold 9 can vary by embodiment and may include one or more solenoid valves, piezoelectric valves, air piloted valves, rotary valves, cam actuated valves, and/or diaphragm valves. In some embodiments, the feed/waste valves may be decoupled from the compressor assembly 2, adsorbers of the gas separation system 3, and other structural components to reduce transmission of noise from the valves to other system components or the exterior of the oxygen concentrator system 100. A valve fluid path may be connected with compliant members to achieve an appropriate level of mechanical isolation, and the feed/waste manifold 9 or valve mounting can be additionally isolated from other components. Alternatively, in some embodiments, the valves may be directly mounted to relatively high-mass, high density components, such as a compressor head of the compressor assembly 2 or the adsorbers of the gas separation system 3 to reduce noise transmission. These components may also then be isolated from other components in the system, particularly large plastic bodies such as housings or chassis components. The feed/waste valves contained in feed/waste manifold 9 can additionally direct exhaust nitrogen-rich gas from the adsorbers of the gas separation unit 3 to a muffler in a pressure swing adsorption (PSA) system or to a vacuum pump in a vacuum swing adsorption (VSA) or vacuum pressure swing adsorption (VPSA) system.

In some embodiments, the adsorbers of the gas separation system 3 are designed to be removable and replaceable as described in the above incorporated references. Each adsorber can include an adsorbent material and a vessel housing the adsorbent material. The adsorbent material can be in the form of an adsorbent bed. The adsorbent bed may contain at least one pretreatment adsorbent layer that is directed to water and carbon dioxide removal to prevent contamination of a main layer adsorbent. In some embodiments, this material may be a desiccant such as activated alumina or silica gel. In alternate embodiments, the pretreatment layer may contain a sodium or lithium exchanged zeolite. The adsorbent bed can also include a main layer adsorbent that is directed to separate oxygen from nitrogen in ambient air. The main layer adsorbent may be a lithium exchanged zeolite material. Nitrogen is retained in the adsorber, while oxygen-rich gas is allowed to pass through the adsorber into the product valves or product valve manifold 10.

The product valve manifold 10 may include one or more of solenoid valves, piezoelectric valves, air piloted valves, rotary valves, cam actuated valves, or diaphragm valves, check valves, and orifices to control gas flow. The product valve manifold 10 connects to the adsorbers of the PSA gas separation system 3 and may be decoupled from the adsorbers and other structural components to reduce noise transmission and vibration between valves and other components in the system. The product valve manifold 10 may also be part of a common assembly with the feed/waste valve manifold 9 with appropriate portions of the valve directing gas into and out of the adsorbers.

In some embodiments, oxygen-rich gas flows from the product valve manifold 10 to an integrated assembly that is directed to product gas storage 4, oxygen gas concentration measurement, oxygen gas pressure and temperature sensing, as well oxygen gas filtration, and oxygen gas delivery, e.g. a gas delivery system 7. In some embodiments, the gas delivery system 7 can be a conserver. In some embodiments, the integrated assembly contains multiple sensors 11 for various functions including ambient pressure sensing, oxygen gas pressure measurement, breath pressure or cannula pressure measurement, and temperature measurement.

The control of the oxygen concentrator system 100 can be achieved by a programmable controller 5. The oxygen concentrator system 100 also may contain a user/data interface 8. The user/data interface 8 can include one or more buttons or other inputs to control various features or functions of the concentrator system 100 such as, for example, power state, oxygen flow rate, and or any other concentrator system function. Other embodiments additionally contain an LCD display, at least one removable and rechargeable battery, and an integrated oxygen conserving device to deliver oxygen gas synchronously with a patient's onset of inhalation to maintain clinical efficacy while reducing the amount of oxygen-rich gas delivered to the patient by a factor of about 2:1 to 9:1.

Figure 1B:
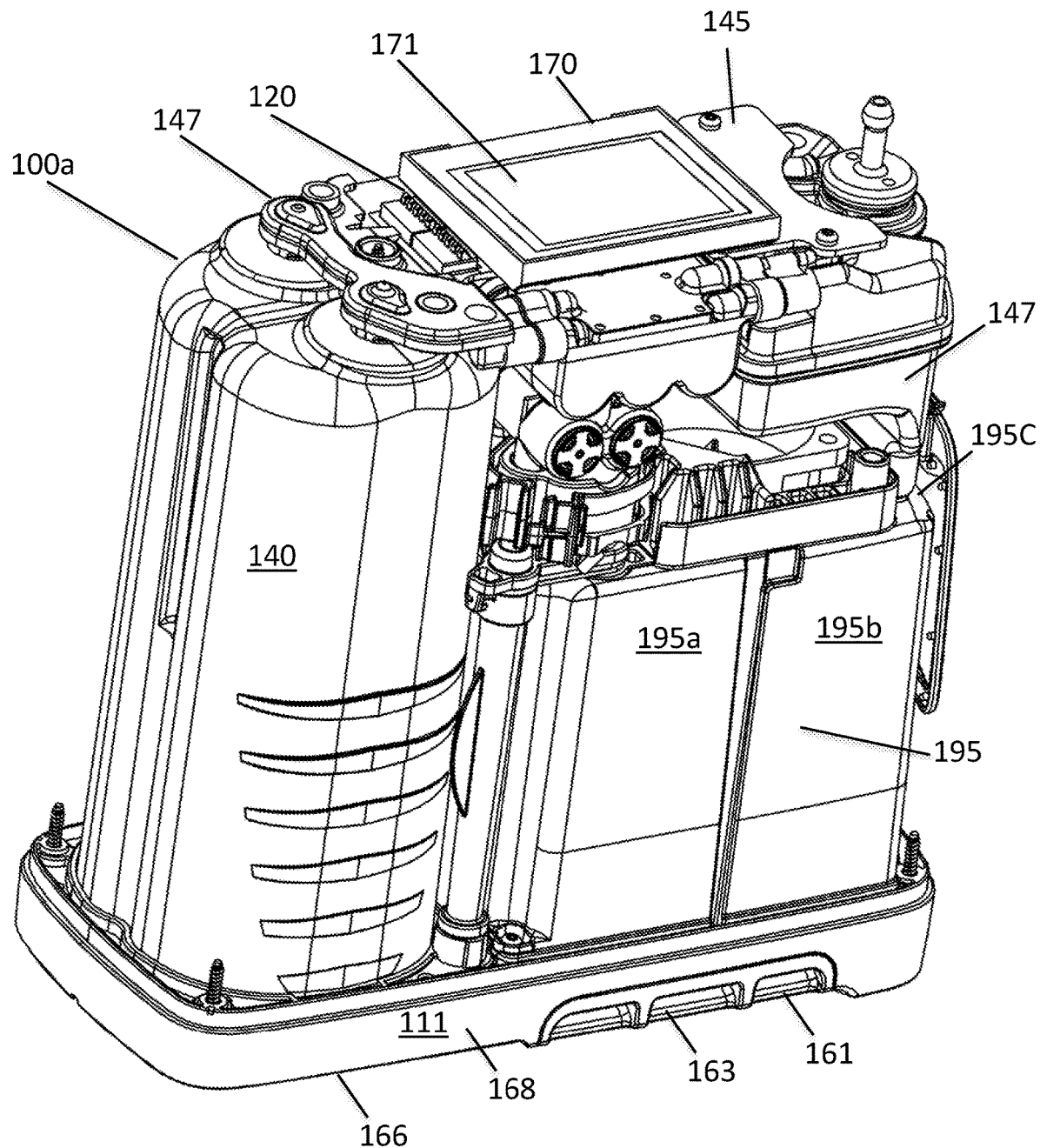
FIG. 1B shows an isometric view of internal components of one embodiment of an exemplary portable oxygen concentrator.
Figure 1C:
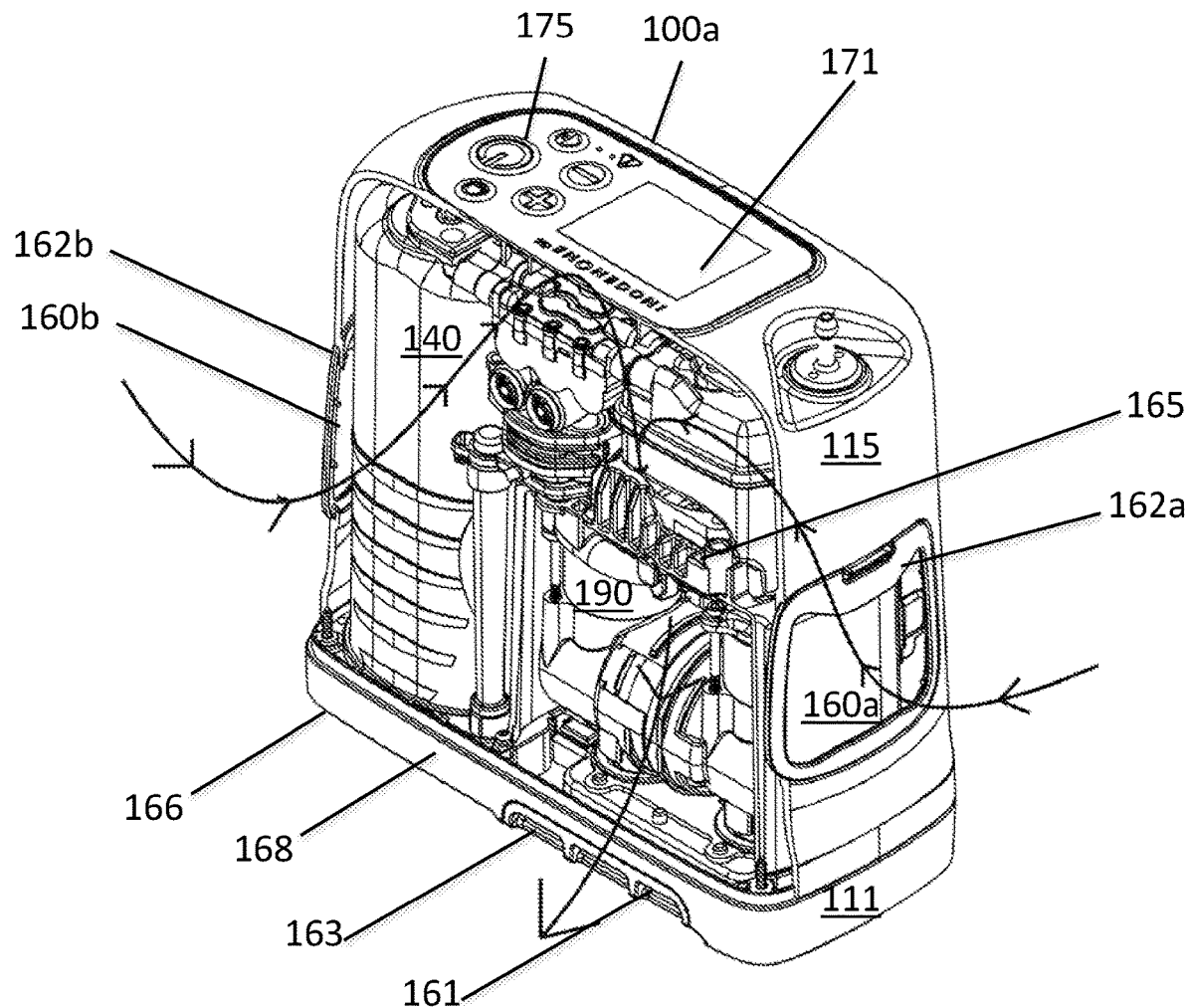
FIG. 1C shows a cutaway isometric view of the internal components of one embodiment of an exemplary portable oxygen concentrator illustrating internal air flow.

FIGS. 1B-1E and FIG. 2 illustrate an embodiment of the oxygen concentrator system disclosed herein in the form of a portable oxygen concentrator 100a. The concentrator system 100a can include any of the same or similar features and functions as the concentrator system 100. FIGS. 1B and 1C are interior isometric views taken from two opposing sides of the oxygen concentrator 100a. As shown in FIG. 1B, the portable oxygen concentrator 100a includes a dual function chassis base 111. The chassis base 111 can serve as a support for the internal components of the oxygen concentrator 100a. The chassis base 111 can also serve as a mount for a power source, such as a battery.

As shown in FIGS. 1B and 1C, the portable oxygen concentrator 100a further includes one or more adsorbers 140 positioned on one end of the chassis base 111, a compressor assembly 190, and a shell structure 195. In some embodiments, the adsorbers 140 are non-cylindrical adsorbers. The vessels forming the adsorbers 140 can be generally non-cylindrical in shape.

Figure 2:
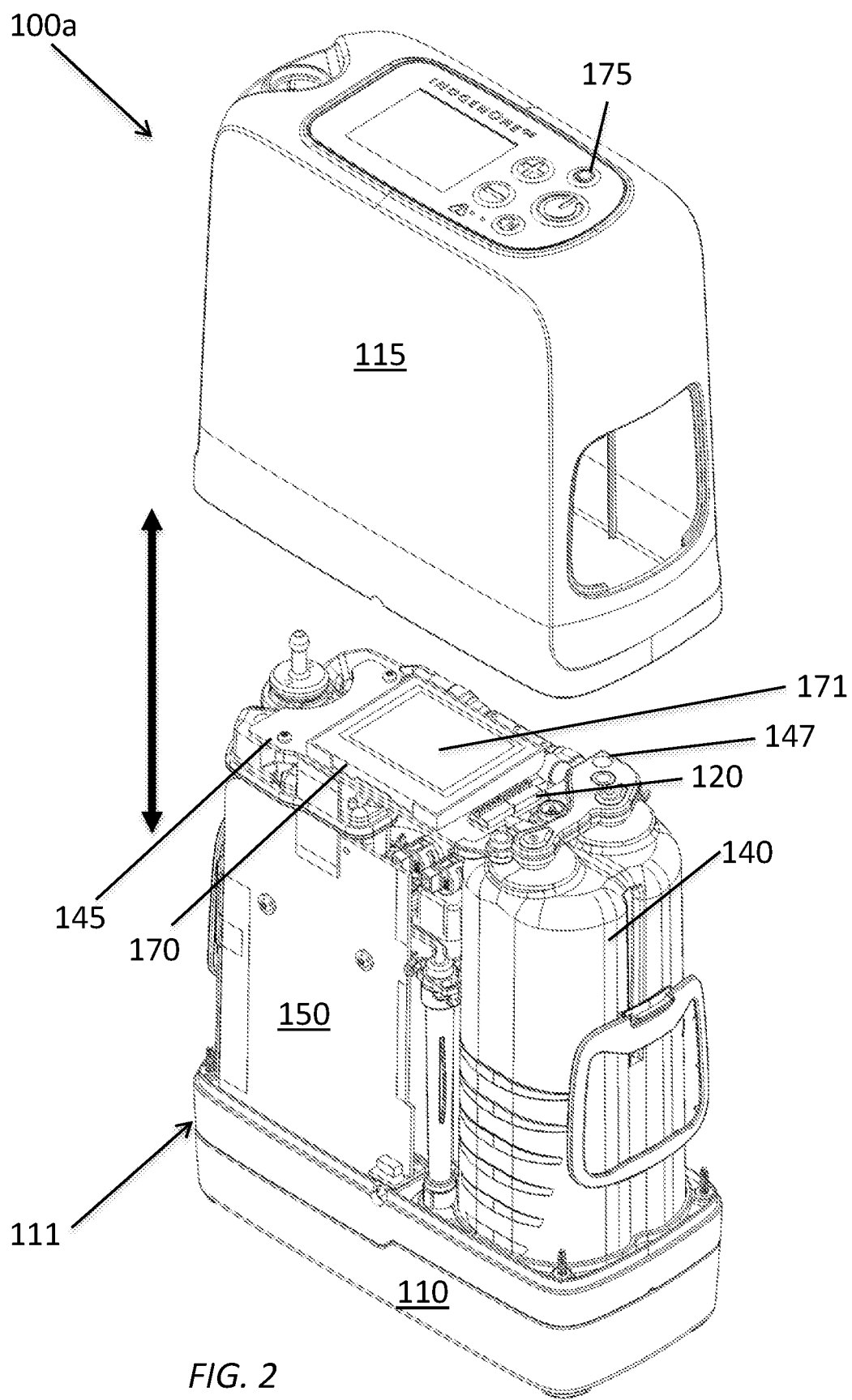
FIG. 2 shows an isometric view of one embodiment of an exemplary portable oxygen concentrator with a removable external housing.

As shown in FIG. 1C, the oxygen concentrator 100a includes an outer housing 115 coupled to the chassis base 111 so as to define an internal volume enclosing elements of the concentrator system 100a, such as the adsorbers 140, an airflow generator 165, the compressor assembly 190, and the shell structure 195. In some embodiments, the shell structure 195 can include one or more insulating panels 195a-c disposed about the compressor assembly 190. In some embodiments, the shell structure 195 can surround the compressor assembly 190. In some embodiments, the shell structure 195 is configured to separate the cooling airflow in the oxygen concentrator system 100a from the higher temperature, spent airflow adjacent the compressor assembly 190 that is ready to be expelled from one or more exhaust outlets or ports 161. In some embodiments, the shell structure 195 forms at least a portion of an enclosure or at least partially sealed chamber around the compressor assembly 190. In some embodiments, insulating panels 195a-c can be disposed adjacent the compressor assembly 190, for example, in an angled arrangement, which together with the other components surrounding the compressor assembly 190 (e.g., printed circuit board) form an enclosure or at least partially sealed chamber that impedes or prevents heat transfer from the higher temperature, spent airflow to the cooling airflow. In some embodiments, a printed circuit board, such as printed circuit board 150 as shown in FIG. 2, can form at least a portion of an enclosure or at least partially sealed chamber around the compressor assembly 190. In some embodiments, an interior surface of the housing 115 can form at least a portion of an enclosure or at least partially sealed chamber around the compressor assembly. In some embodiments, the shell structure 195 can separate the compressor assembly 190 from one or more other elements positioned within the internal volume defined by the housing 115, such as the adsorbers 140.

The portable oxygen concentrator 100a further includes one or more pneumatics modules, sensor modules, and display modules. As shown in FIGS. 1B-C, in some embodiments, the one or more pneumatics modules, sensor modules, and display modules can be formed as a combined upper pneumatics, sensor, and display module 145 that can be detachably removed as a unit. In some embodiments, the shell structure 195 can separate the compressor assembly 190 from one or more pneumatics modules, one or more sensor modules, one or more electronic modules, or other elements of the concentrator system.

The oxygen concentrator 100a further includes one or more user interface controls 175, a control electronics printed circuit board (PCB) (not shown), one or more electrical connectors 120 adapted to mate with connectors coupled to the housing 115, and a printed circuit board (PCB) 170. The printed circuit board 170 can be a user interface display/sensor PCB or sensor block PCB, or include both. The printed circuit board (PCB) 170 can include various control sensors such as oxygen purity, pressure, and temperature sensors. In some embodiments, the printed circuit board 170 can include or be coupled to a user interface display 171. In some embodiments, the upper pneumatics, sensor, and display module 145 includes an interface manifold 147 that can be removably attached to an end of the adsorbers 140 and the product manifold. In some embodiments, the control sensors can be electrically connected to the interface. In some embodiments, the shell structure 195 in combination with the PCB 150 and a top portion of the housing 115 can enclose the compressor assembly 190 in a chamber or "hot box" in which hot air is retained, for example, by creating an enclosure or at least partially sealed chamber around the compressor assembly 190. This chamber or hot box can separate airflow from an airflow generator, such as a fan or blower, into hotter air adjacent the compressor and cooler air outside the hot box.

FIG. 1C shows an implementation of the cool to hotter airflow control as described above. In this airflow implementation, an airflow generator 165 is mounted directly over the compressor assembly 190. The airflow generator 165 can be a blower or fan. The outer housing 115 can include one or more air inlets 160a-b. The air inlets 160a-b can be recessed within the outer housing 115 or extend along a curved or angled surface of the outer housing 115. In some embodiments, the air inlet 160a and the air inlet 160b can be positioned on different faces or surfaces of the outer housing 115. In some embodiments the air inlet 160a and the air inlet 160b can be positioned on opposite surfaces of the outer housing 115. Air can be drawn in from two sides of the oxygen concentrator 100a through the air inlets 160a and 160b disposed on opposing sides of the oxygen concentrator 100a. In alternative embodiments, the air inlet 160a and the air inlet 160b can be positioned on the same face or surface of the outer housing 115. In some embodiments, internal components can be positioned such that cooler outside air flows over most of the internal components before being directed to the vicinity of the compressor assembly 190.

The airflow generator 165 is configured to direct airflow along an airflow path between the one or more air inlets 160a-b and one or more exhaust outlets or ports 161. In some embodiments, one or more exhaust ports 161 can be positioned within the chassis base 111. In some embodiments, the chassis base 111 can include exhaust ports 161 on opposite side surfaces of the chassis base 111. Both exhaust gas from the PSA gas separation unit and the fully downstream spent cooling gas are exhausted through exhaust ports 161 on each side of chassis base 111. In alternative embodiments, the exhaust ports 161 can be positioned on the same side of the chassis base 111. In some embodiments, higher temperature, spent cooling airflow is confined to the area surrounding the compressor assembly 190 and exhausted immediately adjacent the bottom of the compressor assembly 190. This is an example of a push/pull airflow in which the compressor assembly 190 is positioned at a downstream end of the airflow path immediately before the exhaust ports 161. Such an arrangement can accomplish the delivery of cool air to many of or most of the internal components before exhausting hot air from the higher temperature components in the vicinity of the compressor assembly 190. In some embodiments, it is desirable to exhaust hot air in the vicinity of the compressor assembly as soon as possible, for example, to reduce backflow of the higher temperature air from the vicinity of the compressor assembly 190 to other internal regions of the concentrator 100a. The positioning of the exhaust ports 161 adjacent to the compressor assembly 190 can reduce such a backflow. Advantageously, the cooling air flow path of the oxygen concentrator system 100a ends at an area adjacent the component that generates the most heat, for example, the compressor assembly 190, so that the spent cooling air can be expelled before affecting other components.

The oxygen concentrator 100a is configured to minimize the likelihood of impeding the airflow through the device in as many use situations as possible such as, for example, placing the oxygen concentrator 100a against a flat vertical surface or laying the concentrator 100a on its side (other than the intended bottom side). The air inlets 160a and 160b are designed and arranged to substantially reduce the risk of inlet vent obstruction. The exhaust ports 161 are contoured such that they cannot be blocked by any single plane. In one embodiment, the exhaust ports 161 are disposed on only one side of the chassis base 111 such that the ports 161 directs hot exhaust gas away from the patient's body when the oxygen concentrator 100a is being carried adjacent to the patient body such as in a shoulder bag or hip bag. In some embodiments, the design of the air inlets 160a-b and/or exhaust ports 161 can include additional geometrical details such as curvature of a face of the air inlets 160a-b and/or exhaust ports 161, recessing of the air inlets 160a-b and/or exhaust ports 161 below the surface of the concentrator housing 115, and/or angling of the exhaust ports 161 to direct both air flow and noise in a desirable direction as it exits the concentrator system 100*a*. In some embodiments, the exhaust ports 161 are angled away from a removable battery 110 coupled to the chassis base 111 to prevent heating of the battery 110. In some embodiments, the exhaust ports 161 can be formed in a portion of the chassis base 111 extending laterally beyond a lateral edge of the battery 110. In some embodiments, the exhaust ports 161 are directed at a downward angle over a recess formed in the portion of the chassis base 111 extending laterally beyond a lateral edge of the battery 110. The angling and positioning of the exhaust ports 161 can prevent obstruction of the exhausts ports 161 if the concentrator is placed against or adjacent a flat surface.

In one embodiment, each air inlet 160*a-b* includes an opening defined by an exterior border 162*a-b* that is recessed from a portion of the exterior surface of the housing 115, which may have a planar or convex contour. In some embodiments, the recessed exterior borders 162*a-b* of the air inlets 160*a-b* in combination with the convex contour of the exterior surface of the housing 115 form an air gap that permits at least some air to flow through even when the exterior surface of the housing is resting against a planar surface such as a table top. In some embodiments, a middle section of each exterior border 162*a-b* is not coplanar with the opposing end sections such that the middle section slightly protrudes from the opposing end sections. In some embodiments, the air inlets 160*a-b* comprise louvers having a curved configuration adapted to increase intake of airflow from multiple directions.

Figure 1D:
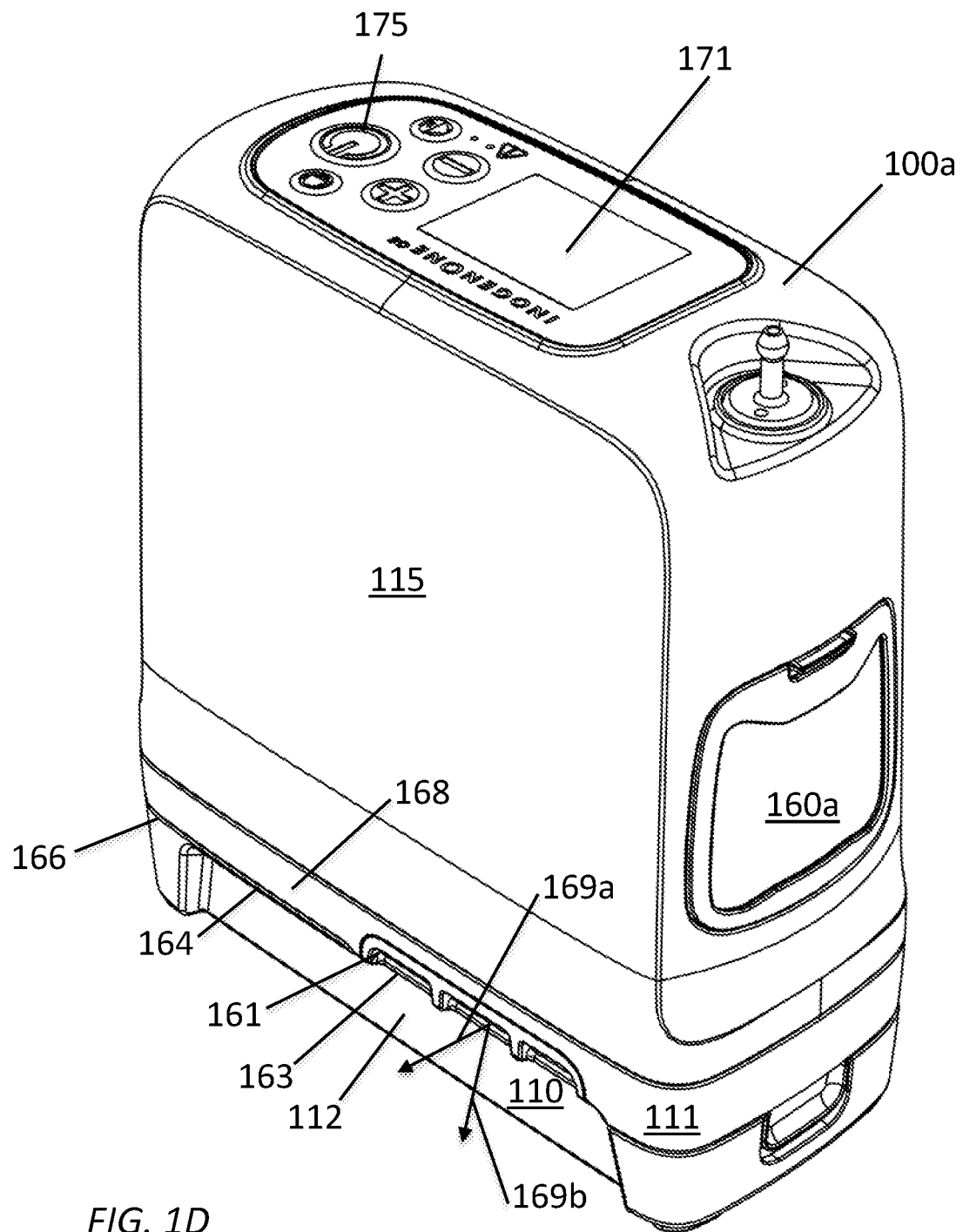
FIG. 1D shows one embodiment of an exemplary portable oxygen concentrator with a battery.
Figure 1E:
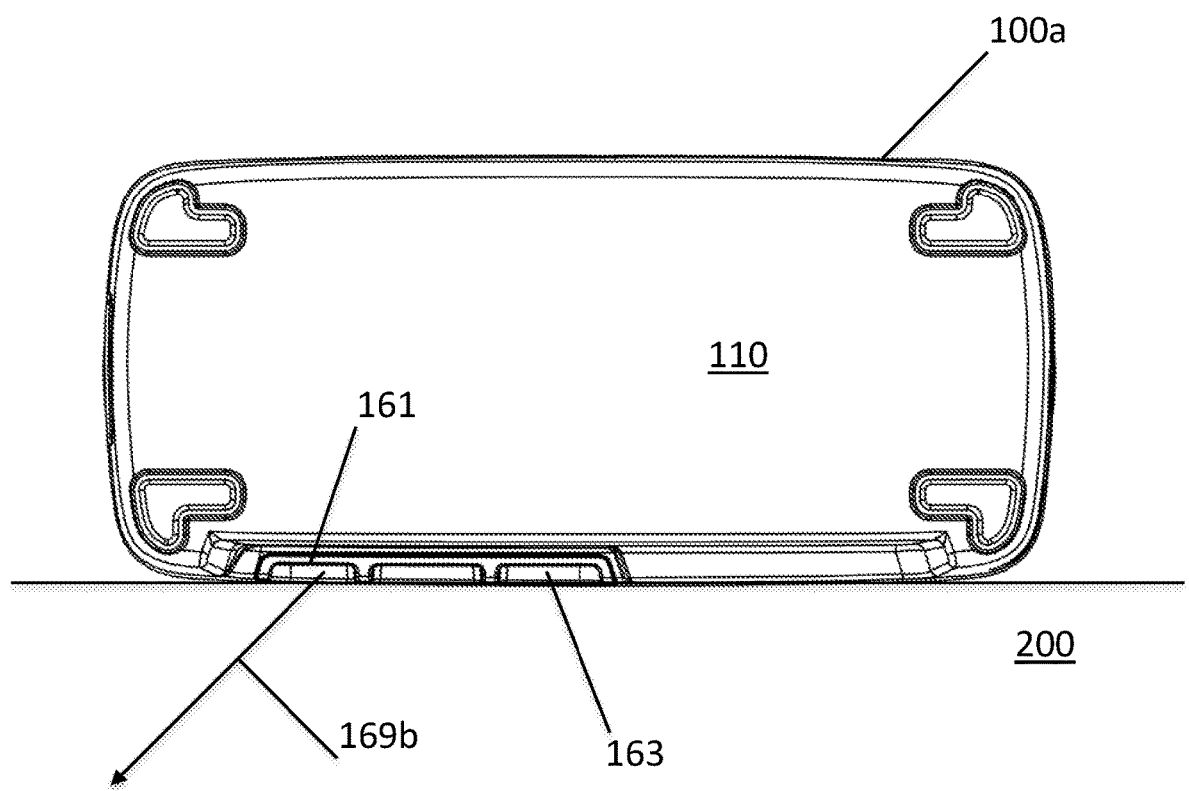
FIG. 1E shows one embodiment of the portable oxygen concentrator of FIG. 1D resting on a side against a flat surface.

FIG. 1D shows the oxygen concentrator 100*a* having the battery 110 slidably mounted to a lower surface 166 of the chassis base 111. As also shown in FIG. 1D, a plurality of the exhaust ports 161 are disposed horizontally along a lower edge 164 of the chassis base 111. Each exhaust port 161 comprises a recessed opening 163 defined by an exterior border that is disposed on the sidewall 168 and lower surface 166 of the chassis base 111. The recessed opening 163 extends into the sidewall 168 and partially into the lower surface of the chassis base 111 so as to form an opening that allows for at least two airflow paths 169*a-b* from the oxygen concentrator. In some embodiments, the airflow paths 169*a* and 169*b* can be offset. In some embodiments, the airflow paths 169*a* and 169*b* can be perpendicular or generally perpendicular. As FIG. 1D further shows, at least a portion of a lateral side 112 of the battery 110 is recessed such that when the battery 110 is mounted to the chassis base 111, the sidewall 168 of the chassis base 111 protrudes outwardly from the recessed portion of the lateral side 112 of the battery 110 thereby exposing the recessed opening 163 of each exhaust port 161. Additionally, the battery recess near the exhaust ports 161 provides additional space for the exhaust gas heat to dissipate with minimal contact to the battery housing, which minimizes the amount of exhaust gas heat which may be transferred to the battery 110. Minimizing battery heating is advantageous to battery performance and life, particularly if the heat is specific to a portion of the battery such as the small region surrounding the exhaust outlets. FIG. 1E shows the oxygen concentrator 100*a* resting against a flat surface 200 on the side where the exhaust ports 161 are located. As shown in FIG. 1E, the recessed openings 163 of the exhaust ports 161 are not obstructed even though the side with the exhaust ports 161 is resting against a planar surface. The configuration of the exhaust ports 161 in combination with the battery design enable air 169*b* to still flow out of the exhaust ports 161. In one embodiment, the exhaust ports 161 comprise louvers having a configuration adapted to direct air to flow in an angled direction. Combined, these features increase the likelihood of full or partial air flow helping to prevent overheating even if the oxygen concentrator 100*a* is improperly positioned during use.

As described in co-pending application Ser. No. 15/608,775, one way to implement a portable oxygen concentrator package is to mount the internal workings, e.g., the adsorbers, valves, compressor and controller elements to a chassis and cover the chassis and internal elements with a removable outer housing. Such an arrangement is shown in FIG. 2. The outer housing 115 is configured to removably couple to the chassis base 111. As shown in FIG. 2, the outer housing 115 contains user interface elements including one or more user interface controls 175. The user interface controls 175 can be electrically connected to the PCB 170. The PCB 170 can be mounted to a superior end of the chassis base 111. In addition, as shown in FIG. 2, the interior components of the oxygen concentrator 100*a* are designed and arranged in a manner such that the overall exterior contour created by the interior components substantially conforms to the rectangular shaped outer housing 115 so as to reduce waste of space inside the housing 115. For example, the two adsorbers 140 positioned on one end of the chassis form an exterior contour containing somewhat flattened sides with rounded corners to mirror the configuration of the outer housing 115. The PCB 150 is positioned in a vertical orientation along a lateral side of the chassis to mirror the flat lateral side of the outer housing 115.

Figure 3A:
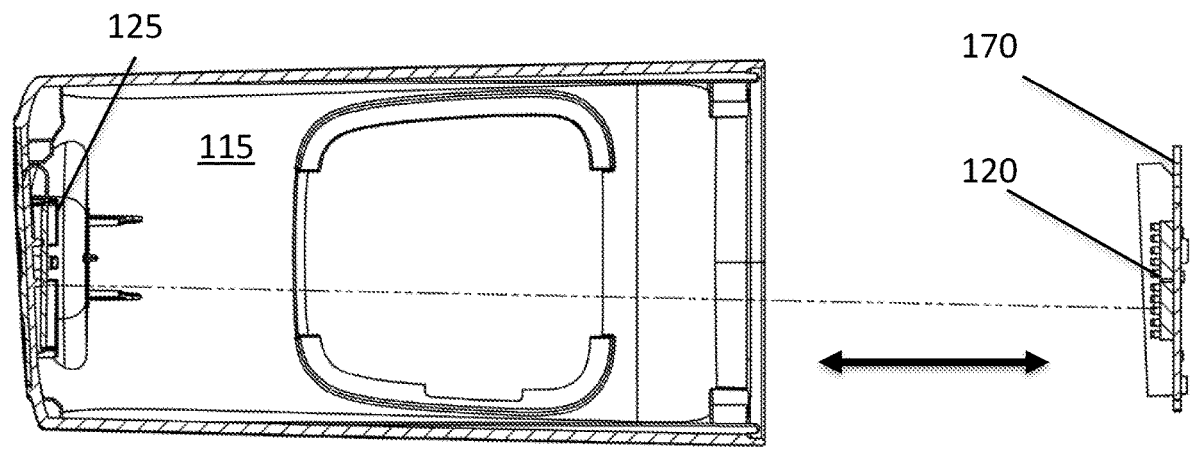
FIGS. 3A and 3B show an illustrative embodiment of an interconnect system between the outer housing and the concentrator chassis of one embodiment of an exemplary portable oxygen concentrator.
Figure 3B:
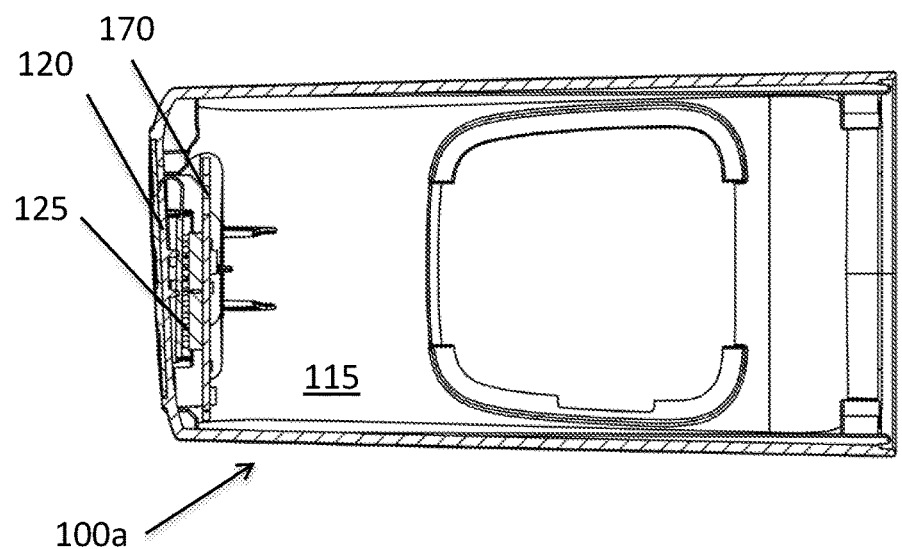

FIGS. 3A and 3B show an improved design for making the electrical connection between the outer housing 115 and the interior components of the oxygen concentrator 100*a*. As shown in FIG. 3A, the outer housing 115 can include one or more electrical connectors 125 in electrical communication with the electrical components of the outer housing 115, such as the user interface controls 175. The electrical connectors 120 can reside on the PCB 170. The electrical connectors 125 can be positioned to align with and mate with the electoral connectors 120 when the outer housing 115 is coupled to the chassis base 111.

The outer housing 115 can be configured to define an enclosed volume around the printed circuit board 170 when coupled to the chassis base 111. The outer housing 115 can be configured to seal the printed circuit board from external moisture when coupled to the chassis base 111.

The connectors 120 can be oriented on the PCB 170 so as to face in a generally superior direction. The connectors 125 can be positioned on an interior surface of a top wall of the housing 115, and may be oriented to face in a generally inferior direction. During assembly of the oxygen concentrator 100, the outer housing 115 can be traversed generally inferiorly over the internal components of the oxygen concentrator 100 and mated with the chassis 111. These connectors are disposed such that when the outer housing 115 is mated to chassis 111, connectors 120 and 125 mate. This arrangement can facilitate ease of manufacture and improved sealing of the housing 115 and chassis 111. This arrangement allows for establishment of an electrical connection and a mechanical connection without requiring additional external openings in the outer housing that could provide access to moisture.

Figure 4A:
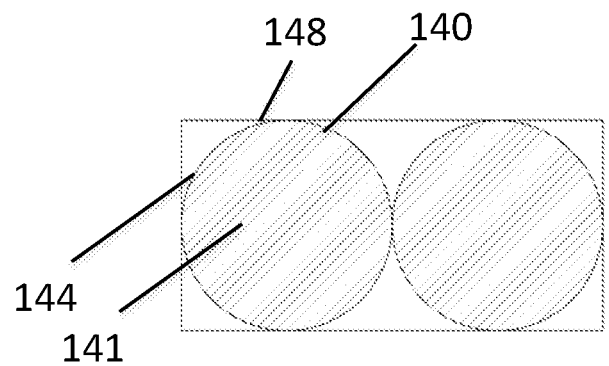
FIGS. 4A through 4D, 5A, and 5B show an illustrative embodiment of gas separation adsorber assembly of an exemplary portable oxygen concentrator.
Figure 4B:
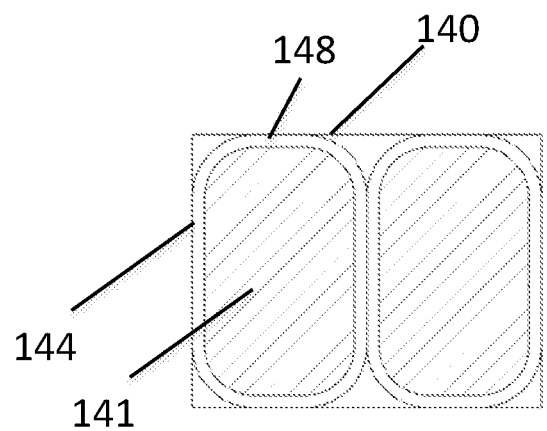
Figure 4C:
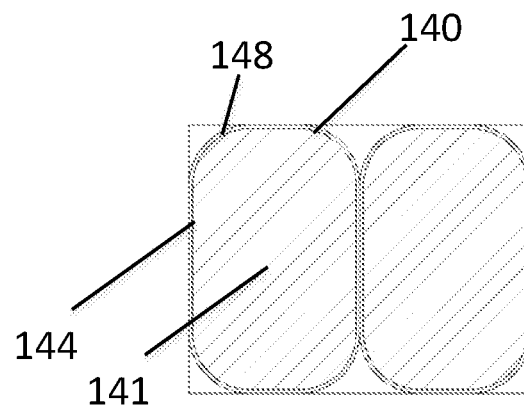

One of the drivers in making a portable oxygen concentrator as small and light as possible is to optimize the operation of the adsorbers 140 of the PSA gas separation unit 3. In general, each adsorber 140 contains an adsorbent material 141 that filters at a molecular level. In some embodiments, the adsorbent material 141 is in the form of an adsorbent bed. In some embodiments, the adsorbent material 141 can filter between nitrogen and oxygen molecules in a manner described above and otherwise employed in gas separation devices including portable oxygen concentrators. In some embodiments, the adsorbent material 141 can include adsorbent particles. Many conventional portable oxygen concentrators utilize zeolite beads for this molecular filter material. These adsorbent particles are densely packed into an adsorbent bed vessel or pressure vessel 144. The vessel 144 and the adsorbent material 141, possibly in combination with other components, can form the adsorber 140. To work effectively and achieve reasonable operational lifetimes, it is important that the adsorbent particles are packed closely and are constrained from movement during PSA cycles when the adsorbers 140 may be subject to zero to 10's of PSI over the course of a few seconds. Portable oxygen concentrators typically utilize adsorbers 140 having vessels 144 with circular cross-sections, such as those shown in FIG. 4A, for example, because a circular cross section allows for thin vessel walls 148 with no or little deformation, keeping the adsorber designs light while ensuring rigidity. However, many oxygen concentrator housing 115 shapes are rectangular solids, typically with some curvature. As shown in FIGS. 4A, 4B, and 4C, a circular cross section vessel 144 is not an efficient way to maximize capacity if the circular columns have to fit into a more or less rectangular shape.

In some embodiments, vessels 144 having non-circular cross sections are used. However, once a vessel 144 design deviates from a circular cross-section, the surfaces, particularly any resulting flat surfaces are more prone to deformation under pressure. One way to counteract potential deformation is to utilize thicker vessel walls 148 as shown in FIG. 4B. However, thicker vessel walls 148 may diminish the advantage in space gained by using the non-circular cross-section shape and add weight rather than performance to the oxygen generating system.

Figure 4D:
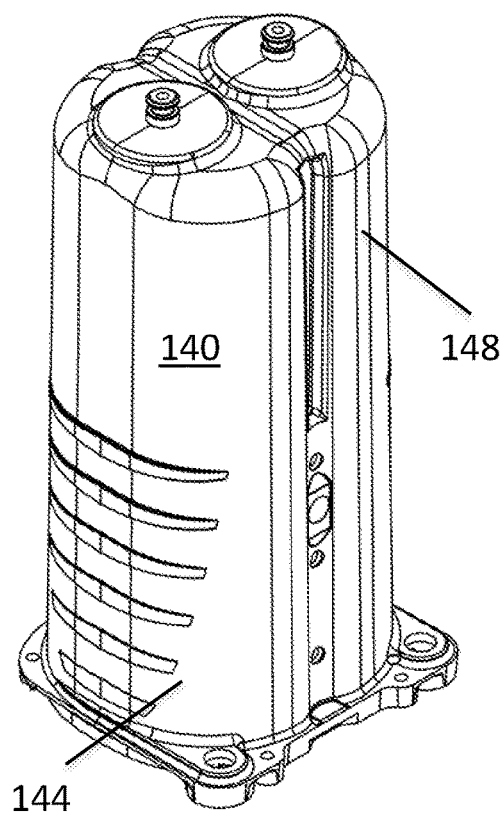

FIG. 4D shows a vessel shape tailored to utilize most of the space at one end of the outer housing 115 in the oxygen concentrator 100a shown above. The shape of the vessel 144 shown in FIG. 4D is non-circular in cross section. In some embodiments, such a shape can include flat deformation prone surface areas.

Figure 5A:
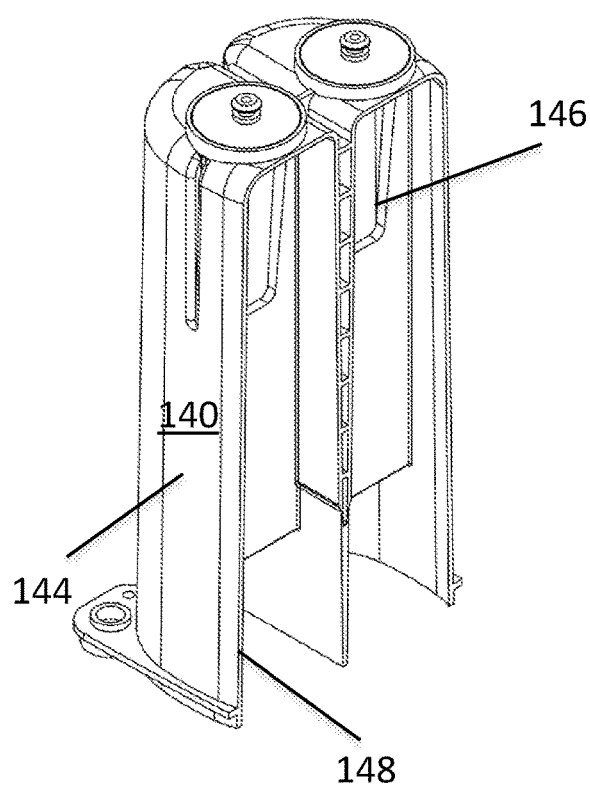

As shown in FIG. 5A, in some embodiments, the adsorbers 140 can include stiffening supports 146 to stiffen the vessel 144 in a direction of likely deformation. In some embodiments, the stiffing supports 146 can be stiffening ribs. In some embodiments, the stiffening supports 146 can extend across an interior of the vessel 144. In some embodiments, the stiffening supports 146 can extend along an interior wall of the vessel 144. In some embodiments, each adsorber 140 can include a single stiffening support 146. In some embodiments, each adsorber 140 can include a plurality of stiffening supports 146. In some embodiments, each adsorber 140 can include one or more stiffening supports 146 extending across an interior of the vessel 144 and/or one or more stiffening supports 146 extending along an interior wall of the vessel 144.

In some embodiments, one or more stiffening supports 146 may alternatively or additionally be added on an exterior portion of the vessel 144. In some embodiments, one or more stiffening supports 146 can be positioned on an exterior surface of the vessel 144.

Adding features to stiffen the structure at the point of deflection can substantially mitigate the deformation with minimum added weight relative to changing the overall wall thickness. In one embodiment, the adsorber system comprises two adsorbers 140 having vessels 144 with oblong, obround, semicircular, or generally semicircular cross-sections joined together. In addition, the non-circular vessels 144 allow more adsorbent material to be placed in the same internal concentrator volume, which in turn increases the oxygen delivery capacity of the oxygen concentrator without increasing the size. In some embodiments, a cross-section of the adsorber 140 can be at least 90% filled with adsorbent material 141. In some embodiments, a cross-section of a portion of the adsorber 140 housing adsorbent material 141 can be at least 90% filled with adsorbent material 141. In some embodiments, the portion of the adsorber 140 filled with adsorbent material 141 can be filled such that at any cross-section of the portion the adsorber 140 is at least 90% filled with adsorbent material 141.

In some embodiments, a combination of a thickness of the vessel wall 148 and a stiffness of the stiffening support 146 is sufficient to limit deformation of the vessel wall 148 to at least one of less than 0.1 mm and less than 25% of an average diameter of the adsorbent particles under a pressure swing of at least 30 psi within the vessel 144. In some embodiments, a combination of a thickness of the vessel wall 148 and a stiffness of the stiffening support 146 is sufficient to limit deformation of the vessel wall 148 to less than 0.05 mm under a pressure swing of at least 30 psi within the vessel 144.

For suitable vessel materials, e.g. materials with suitable stiffness/weight, such as aluminum, magnesium, or plastics materials, it has been found that a combination of wall thickness/support rib stiffness equivalent to achieving maximum deformation of 25% of the adsorbent material particle size under a pressure swing of 30 psi makes possible a shape such as shown in FIG. 4D, an optimized non-circular cross section for a particular shaped volume, with a wall thickness as small as 0.030 inches in a cast magnesium or aluminum material along with strengthening ribs. Other materials and volume shapes may be addressed using similar constraints.

Figure 5B:
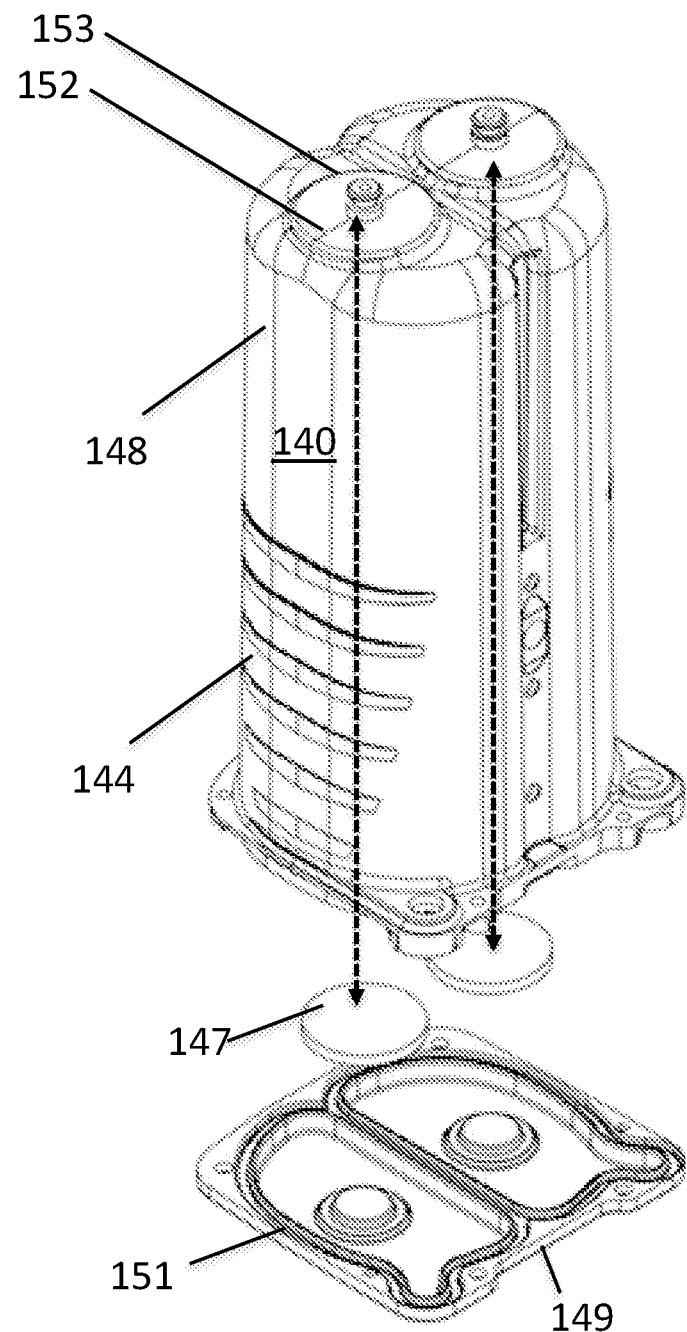

As shown in FIG. 4D-5B, in some embodiments, an adsorber system can include a plurality of adsorbers 140. In some embodiments, the adsorber system can include a first adsorber 140 and a second adsorber 140. In some embodiments, the vessel wall 148 of the first adsorber 140 is joined to the vessel wall 148 of the second adsorber 140. In some embodiments, the vessel wall 148 of the first adsorber 140 is integrally formed with the vessel wall 148 of the second adsorber 140. In some embodiments, the stiffening support 146 of the first adsorber 140 is integrally formed with the stiffening support 146 of the second adsorber 140. As shown in FIG. 5B, in certain embodiments, filters 147 can be recessed within cavities 152 at a superior end of the adsorber 140. In some embodiments, the cavities are defined by the wall 148. In some embodiments, the cavities 152 have a cross-section with a different size and/or shape relative to the inferior portions of the adsorber 140. For example, the cavities can be formed by generally disc-shaped protrusions 153. In some embodiments, the cavities 152 can be formed within protrusions 153 extending from a superior end of the vessel 144. The protrusions 153 can have a cross section different than a cross section of the vessel wall 148. In some embodiments, the protrusion 153 is cylindrical. In some embodiments, the protrusions 153 are integrally formed with the vessel walls 148.

Recession of the filters 147 within the cavities can allow for use of filters or flites having a different shape and/or size relative to the vessel wall 148 of the adsorber 140. For example, recessing the filters 147 within the cavities can allow for use of a round filter or frit with a vessel 144 having a non-circular cross-section.

As shown in FIG. 5B, the adsorber 140 can be sealed at its bottom end via a plate 149 having O-rings 151.

In some embodiments, the walls 148 may have a uniform or variable wall thickness.

As shown in FIG. 2, and shown in co-pending U.S. application Ser. No. 15/608,775, in some embodiments, the battery 110 may act as a suitable base for the portable oxygen concentrator 100 due to its ability to create a low center of gravity for the oxygen concentrator itself.

In previous oxygen concentrator designs produced by the Applicant, a battery has two raised slides in the form of shaped bars extending along part of the length of each side of the battery. The slides can fit into rails on a concentrator chassis base. The slides are placed in the rails, and the battery is slid onto the chassis until electrical connectors from the battery and chassis base are mated and a retainer mating piece contacts a hand actuated retainer. The combination of the mated electrical connector, the relatively long slide/rail connection, and the retainer serves to hold the battery in place within the chassis base. Removal consists of releasing the retainer and sliding the battery out.

Figure 6A:
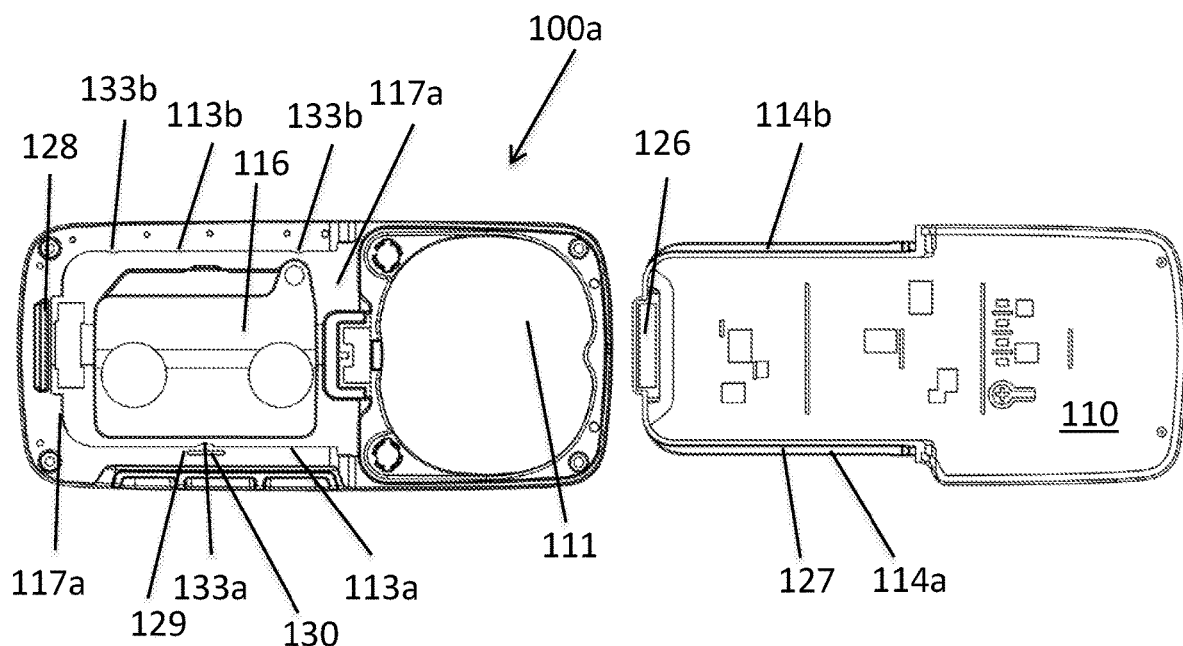
FIGS. 6A through 6D show an illustrative embodiment of a battery retention and alignment assembly of an exemplary portable oxygen concentrator.
Figure 6B:
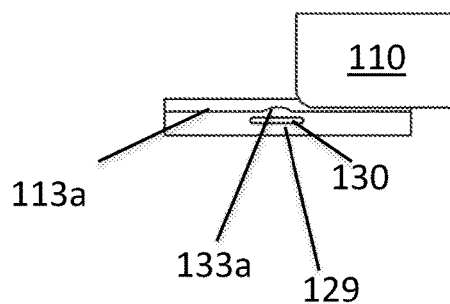
Figure 6C:
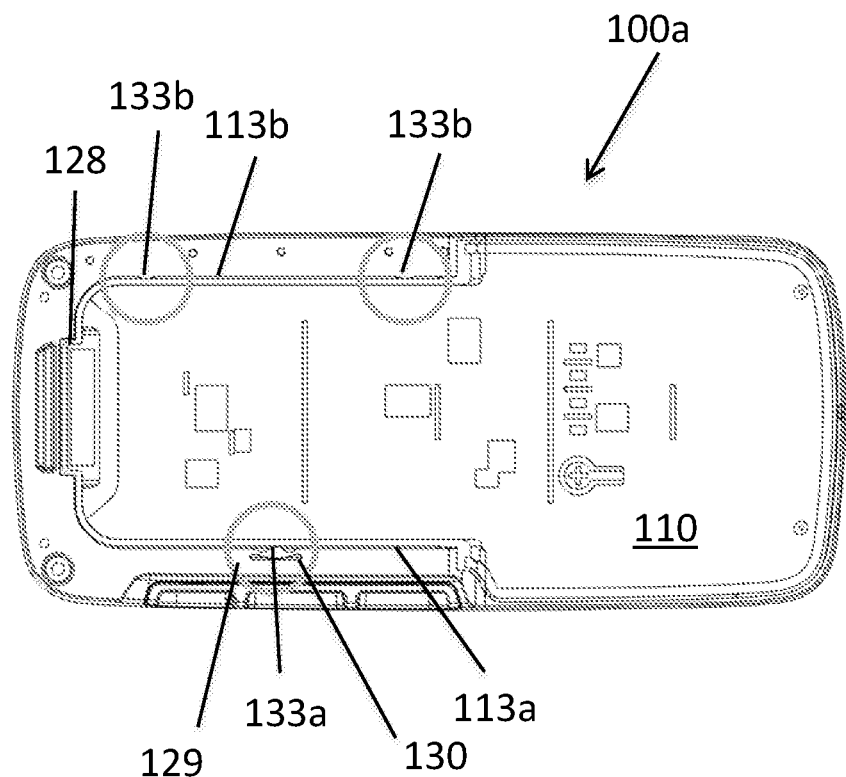

FIGS. 6A-D show an embodiment of an arrangement for securing a battery 110 to a chassis base 111. FIG. 6A shows the battery 110 separated from the chassis base 111. FIG. 6C shows the battery 110 coupled to the chassis base 111.

As shown in FIGS. 6A-D, the oxygen concentrator 100 includes rails 113a-b. The first rail 113a is configured to receive a first slide 114a of a battery 110. The second rail 113b is configured to receive a second slide 114b of the battery 110. The second rail 113b can be spaced apart from the first rail 113a so as to form a channel 116 for receiving the battery 110. The channel 116 can include an open proximal end 117a and a closed distal end 117b.

As shown in FIG. 6A, the rails 113a-b include a flexible stiffening mechanism 129. The flexible stiffening mechanism 129 is configured to impart a biasing force on a surface 127 of the battery 110 when the battery 110 is received in the channel 116.

Figure 6D:
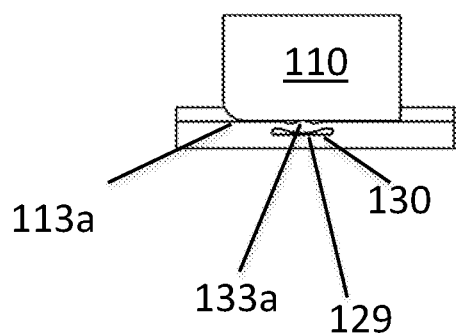

In certain embodiments, the flexible stiffening mechanism 129 includes a bump or protrusion 133a. The protrusion 133a projects from the first rail 113a towards the second rail 113b. The flexible stiffening mechanism also includes a slit 130 positioned behind the protrusion. The slit 130 can be configured to facilitate or allow for travel of the protrusion 133a fore and aft (i.e., towards the second rail 113b or away from the second rail 113b). In some embodiments, the slit 130 can facilitate or allow for flexion of the section of the rail from which the protrusion 133a projections. For example, in some embodiments, the slit 130 can be positioned, shaped, dimensioned, or otherwise configured to allow for movement of the section of the rail from which the protrusion 133a projects. In certain embodiments, the protrusion 133a may alternatively or additionally be deformable so as to facilitate flexion of the protrusion 133a. In certain embodiments, the stiffening mechanism 129 can maintain contact between the first rail 113a and the battery 110 to stabilize the battery 110 within the channel 116, for example, while the battery 110 is inserted into the channel 116 and while the battery 110 is fully seated within the channel 116. FIGS. 6B and 6D depict the flexible stiffening mechanism before and after, respectively, a portion of the battery 110 contacts the flexible stiffening mechanism 129, for example, during an insertion of the battery 110 into the channel 116.

In certain embodiments, the biasing force 110 of the flexible stiffening mechanism 129 is sufficiently flexible to permit translation of the battery 110 within the channel 116 past the protrusion 133a.

Incorporating a flexible stiffening mechanism 129 to the battery attachment of a portable oxygen concentrator 100 can facilitate alignments of smaller and more tightly spaced electrical connections, such as an electrical connector 126 of the battery 110 and an electrical connector 128 of the concentrator 100. In the absence of a flexible stiffening mechanism, at one end of manufacturing tolerances of a battery and a concentrator, some combinations may bind or be difficult for the customer to install. Conversely, at the other end of the manufacturing tolerances, the battery may rattle or cause intermittent or undependable electrical connections between the battery and the concentrator. Use of the flexible stiffening mechanism 129 can facilitate increased stability when using a battery 110 that has a size smaller than an upper tolerance level to reduce installation difficulty. In some embodiments, the flexibility of the stiffening mechanism 129 can facilitate contact between a batteries 110 having different sizes. For example, in some embodiments, the stiffening mechanism 129 can facilitate contact between the first rail 113a and a battery 110 having a size that is smaller than an upper tolerance level of battery sizes capable of being received within the channel 116. As described herein, the increased stability can reduce rattle of the battery 110, for example lateral movement of the battery orthogonal to an axis along which the battery 110 is inserted, and loss of the electrical connections between the battery and concentrator.

In some embodiments, the flexible stiffening mechanism 129 is configured to impart the biasing force on the surface 127 of the battery 110 so as to align the electrical connector 126 of the battery 110 with the electrical connector 128 of the concentrator 100a. By improving alignment of the electrical connections, wear and tear resulting from battery attachment can be reduced.

In some embodiments, one or more protrusions can project from the second rail 113b at least partially towards the first rail 113a. The one or more protrusions projecting from the second rail 113b can be configured to contact the battery 110 when the battery 110 is positioned within the channel 116. In some embodiments, at least one protrusion 133b projection from the second rail 113b is positioned proximally relative to the protrusion 133a. In at least some embodiments, at least one protrusion 133c projecting from the second rail 113b is positioned distally relative to the protrusion 133a. In certain embodiments, the flexible stiffening mechanism 129 is configured to impart the biasing force on the surface 127 of the battery 110 to impart stability to the installation of the battery 110.

In some embodiments, the protrusions 133a-c can form a three point stiffening hold. The protrusions 133a-c can be positioned on the rails 113a-b so that they lightly contact the battery 110 structure when the battery 110 is received within the channel 116. The protrusions 133a-c can be sized to contact the battery 110 when inserted into the channel 116, but also allow the battery 110 to be slid along the rails 113a-b from the open proximal end to the closed distal end, e.g., by providing one or more forces, such as the biasing force of the flexible stiffening mechanism and/or one or more frictional forces, upon the battery 110 of a sufficient magnitude to allow movement of the battery when an external force above a threshold magnitude is applied thereto, but restrict movement of the battery 110 when an external force below a threshold magnitude is applied thereto.

The flexible stiffening mechanism 129 and the protrusions 133b-c can provide an improved coupling of the battery 110 onto the rails 113a-b. This flexion of the stiffening mechanism 129 can achieve better battery engagement and alignment than previous designs without adding space, weight, or cost.

While a single flexible stiffening member 129 on a first rail 113a is described, it is contemplated that a plurality of flexible stiffening members 129 can be employed on one or both of the rails 113a-b. While the flexible stiffening mechanism is described as having a protrusion 133a and a slit 130, other suitable flexible stiffening mechanisms or spring mechanisms may be employed. While two protrusions, protrusions 133b and 133c, on the second rail 113b are described, it is contemplated that one protrusion or more than two protrusion 133b-c can be employed on one or both of the rails 113a-b.

As described herein, portable oxygen concentrators can benefit from designs that are compact in size and internally simple. Due to the flow of gas through a portable oxygen concentration, multiple gas tight interconnections can be required within the interior of the portable oxygen concentrators. Barbed connections are commonly used in portable oxygen concentrators, in which a compliant tube is stretched over a barb on the end of a mating piece. Barbed connections can be limited to small numbers of in line connections both in terms of manufacturability of a two-dimensional arrangement of barbed fittings and in difficulty of installation and removal of tubes from such a two-dimensional arrangement.

Figure 7A:
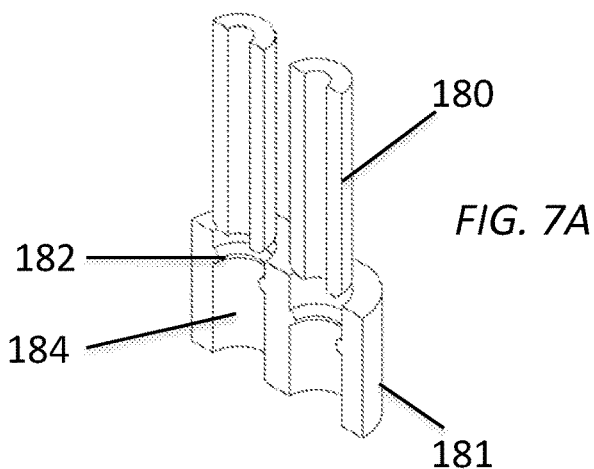
FIGS. 7A through 7K show illustrative embodiments of gas interconnection elements of an exemplary portable oxygen concentrator.
Figure 7B:
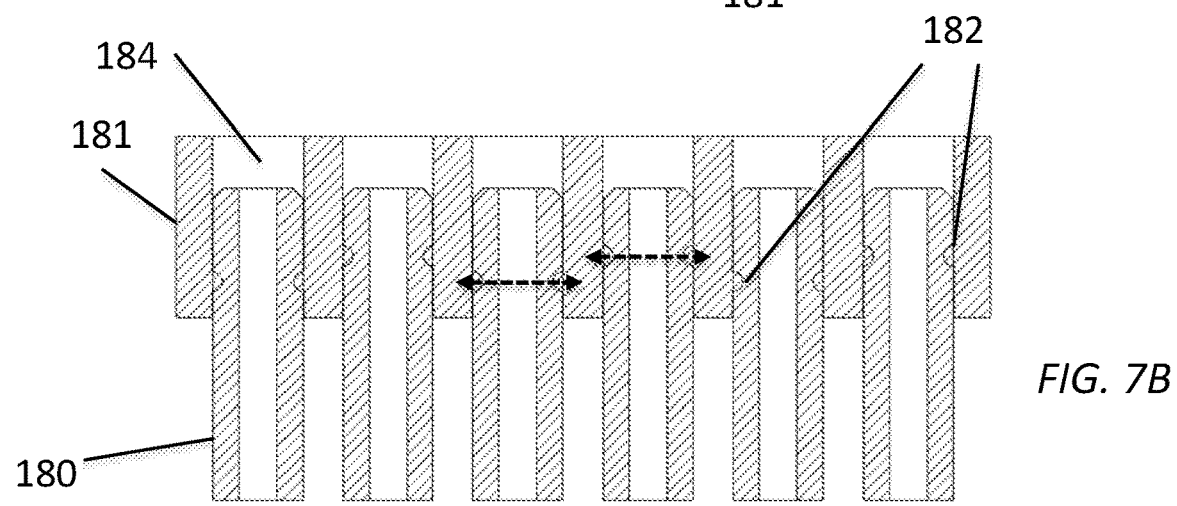
Figure 7C:
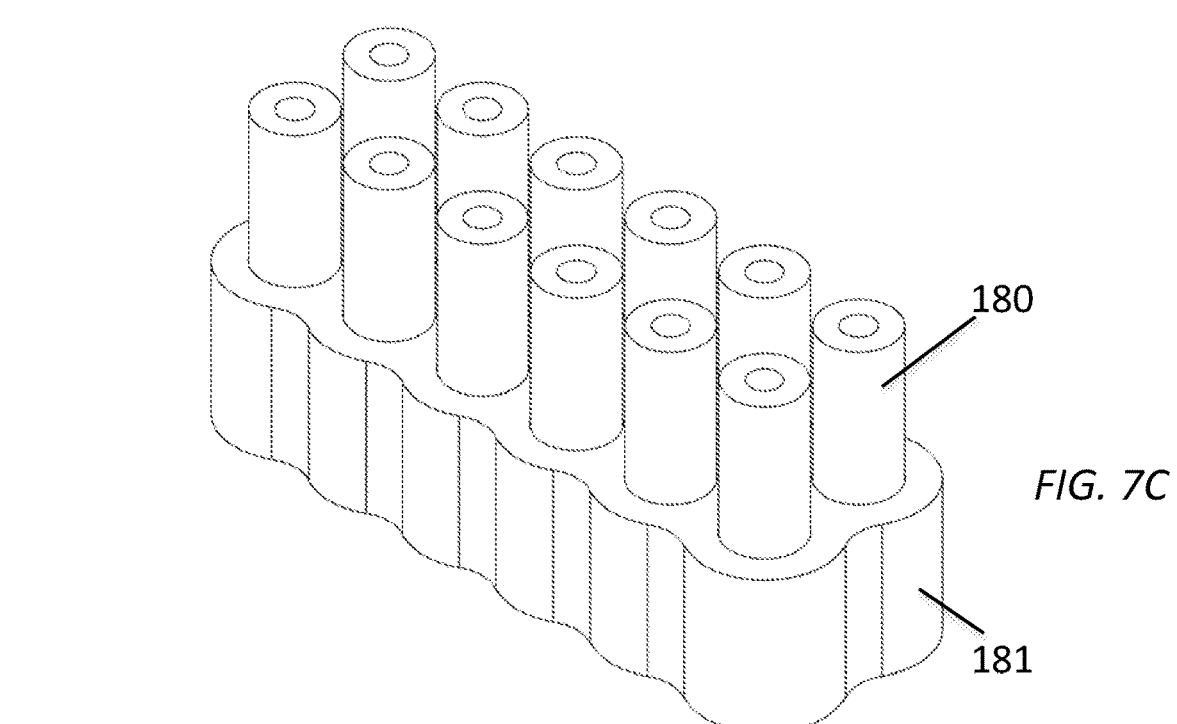

An improved approach to multiple gas connections in one-piece parts is shown in FIGS. 7A-C. A multi-port interconnection 181 is shown in several views with tubes 180 mated thereto. In some embodiments, the interconnection 181 can be compliant or elastomeric. In some embodiments, the interconnection 181 can be formed of a single piece. The interconnection 181 can include a plurality of ports 184, each port configured to receive a tube 180. Each port can include one or more sealing rings 182. In some embodiments, each sealing ring 182 can be in the form of a raised bump on the inside wall of one of the ports 184 of the multi-port connector 181, is employed. Tubes 180 are pressed into the ports 184 of the interconnect 181 until they pass the sealing ring 182. The compression of both the compliant interconnect piece 181 as well as the tubes 180 around the sealing ring 182 provides sealing and/or positioning functions. The raised bump can be circular in some embodiments, but may be any other suitable shape, such as rectangular or triangular. Such an arrangement lends itself to manufacturability and usability for multiple two-dimensional port arrangements such as shown in FIG. 7C.

In some embodiments, compression around the sealing ring 182 of one port 184 can extend into adjacent ports 184 if not addressed. To reduce the spacing required between the ports 184 to achieve a higher density multi-port interconnect 181, in some embodiments, the sealing rings 182 can be positioned at offset locations in adjacent ports 184 as shown in FIG. 7B. Given that the tube sizes in portable oxygen concentrators tend to be on the order of 1 cm in diameter or less, it can be important to keep the density of ports 184 in multi-port interconnect 181 high, for example, so that a multi-port interconnect 181 in the form of a block such as shown in FIG. 7C can make multiple connections between ports 184 and tubes 180 in a space just a few cm in dimension.

Figure 7D:
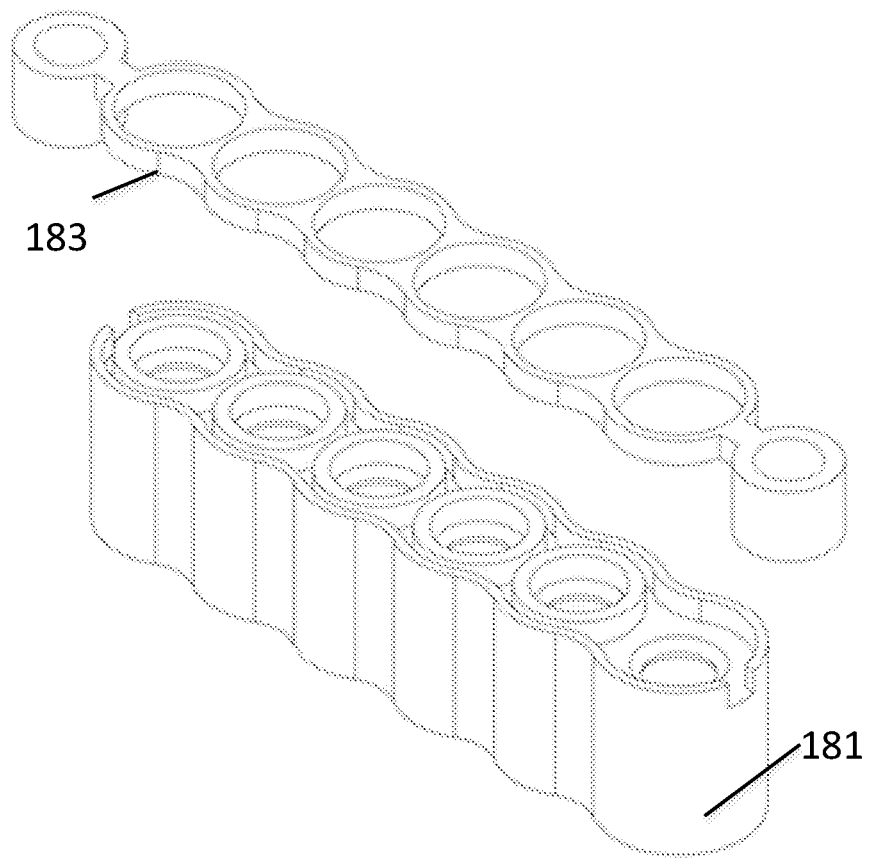
Figure 7E:
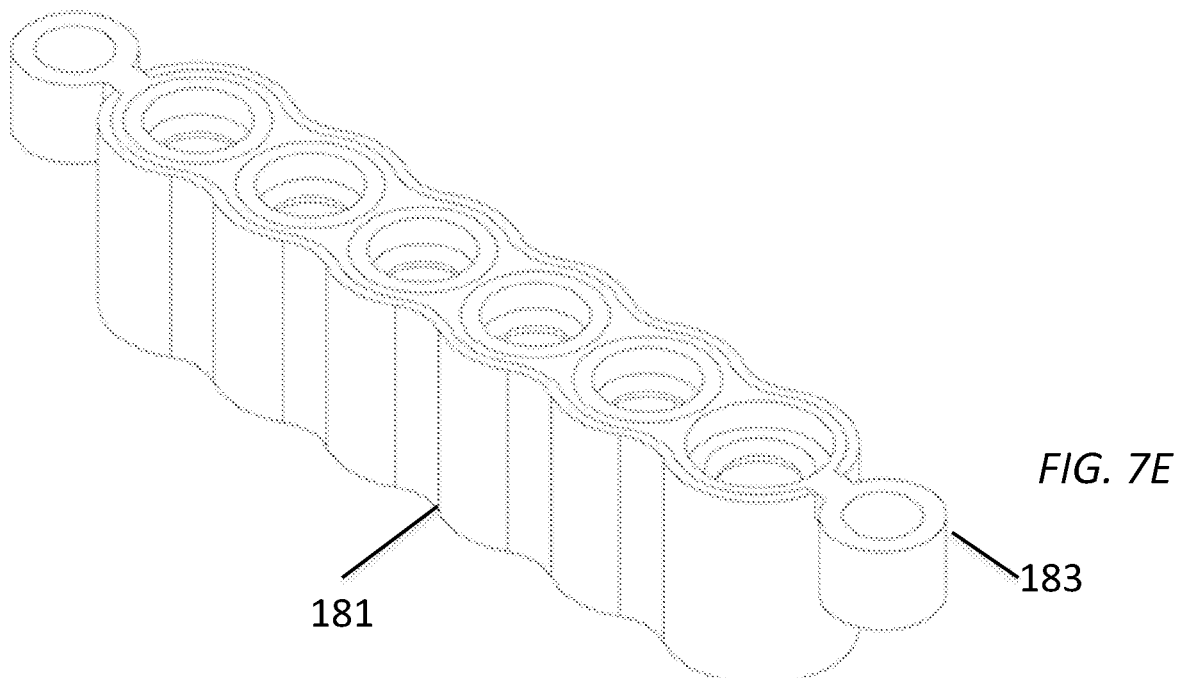

Alternatively, in some embodiments, as shown in FIGS. 7D and 7E, the same or a similar effect can be achieved by use of a non-elastomeric member 183. In some embodiments, a non-elastomeric member 183 can uniformly compress the seal of multiple ports 184 in a single body in the elastomeric element 181. By utilizing a non-compliant or non-elastomeric member 183 that is assembled onto or manufactured into the elastomer 181, uniform compression can be achieved on multiple interconnect ports 184. The addition of the non-compliant member 183 can also allow the use of secondary mounting features such as snap fits, screw bosses, hooks, or simple bosses to maintain the position of the mating parts under pressure. This allows the single member 183 to provide both a pneumatic connection and mechanical position connection in a single component. In some embodiments, the combination elastomeric/non-elastomeric arrangement shown in FIG. 7E can also incorporate sealing ring structures, such as sealing rings 182. The integrally formed multi-port block designs shown in FIGS. 7A-E can provide the sealing and mechanical retention required in a portable oxygen concentrator, but still allow for removal, for repair, or service. In contrast, barb designs employed in other oxygen concentrators can prevent removal of tubes without damage to the tube, barb, or both. In some embodiments, the interconnects 181 shown in FIGS. 7A-E can form a secure connection without requiring secondary retainers such as zip ties or clamps on each individual tube 180. The interconnects 181 can retain many tubes 180 and connections with greatly fewer secondary mounting features than in single port interconnects.

Figure 7F:
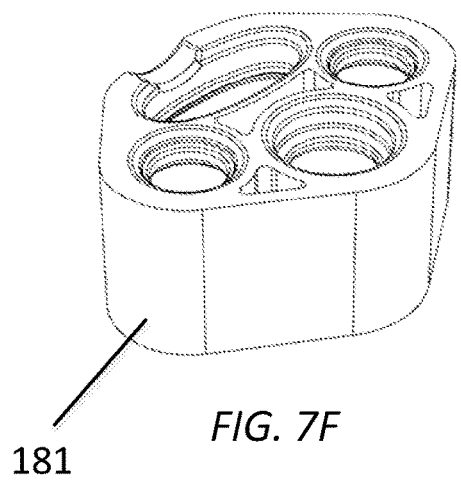
Figure 7G:
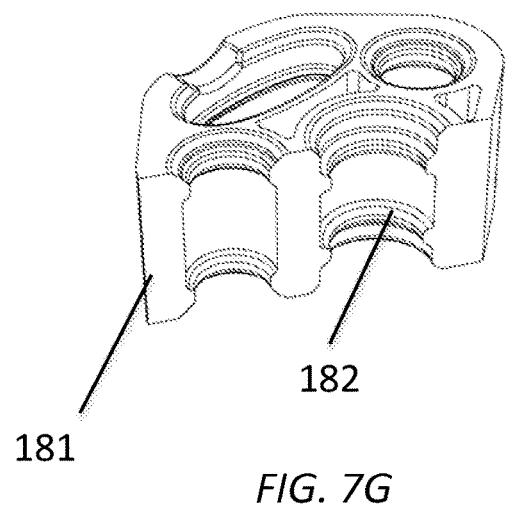
Figure 7H:
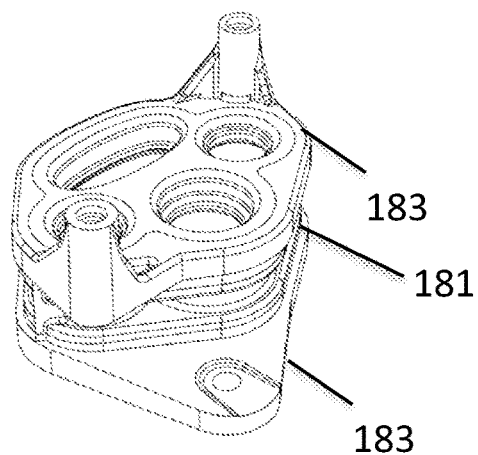
Figure 7I:
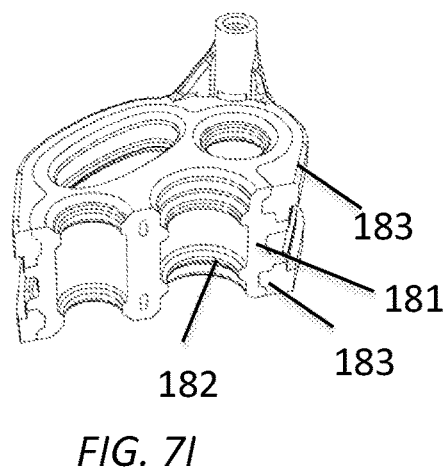

FIGS. 7F and 7G depict an embodiment of an elastomeric multi-port interconnection implementation 181 with four ports and sealing rings 182. As shown in FIGS. 7H and 7I, in some embodiments, two non-elastomeric pieces are molded as described above to form an interconnection element have a compliant interconnect 181 and non-elastomeric pieces 183. In some embodiments, adding non-elastomeric pieces 183 to a compliant interconnect 181 to form an assembly can allow for the use of mounting elements, such as fastener holes, in a more rigid medium than an elastomeric interconnect alone, thus forming an interconnection assembly offering both elastomeric isolation along with secure mechanical mounting. Interconnection assembly elements 181 and 183 may be joined in a variety of ways, including over molding the elastomeric piece to the hard plastic pieces when the elastomeric piece is formed, assembling the components together with mechanical mating features, or bonding the elastomeric piece to the hard plastic pieces.

Figure 7J:
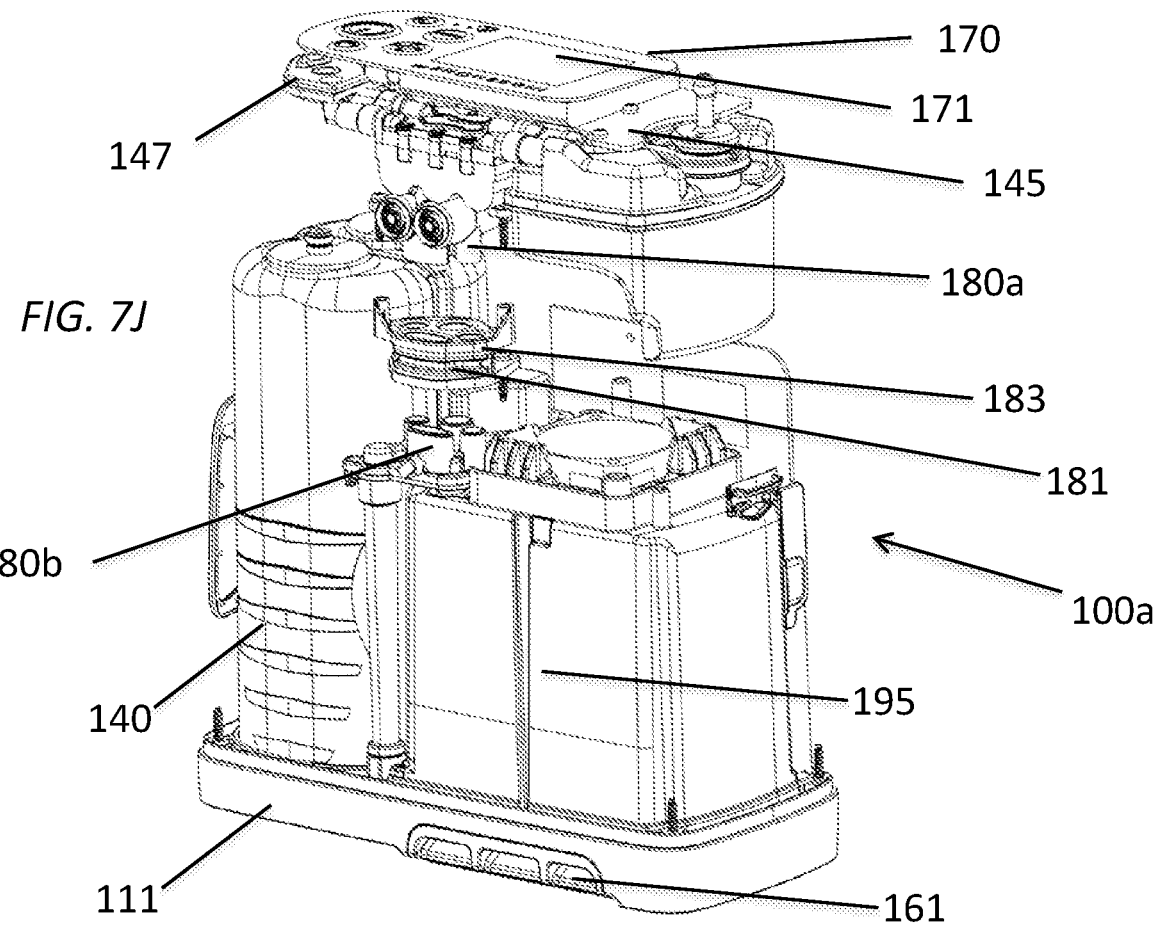
Figure 7K:
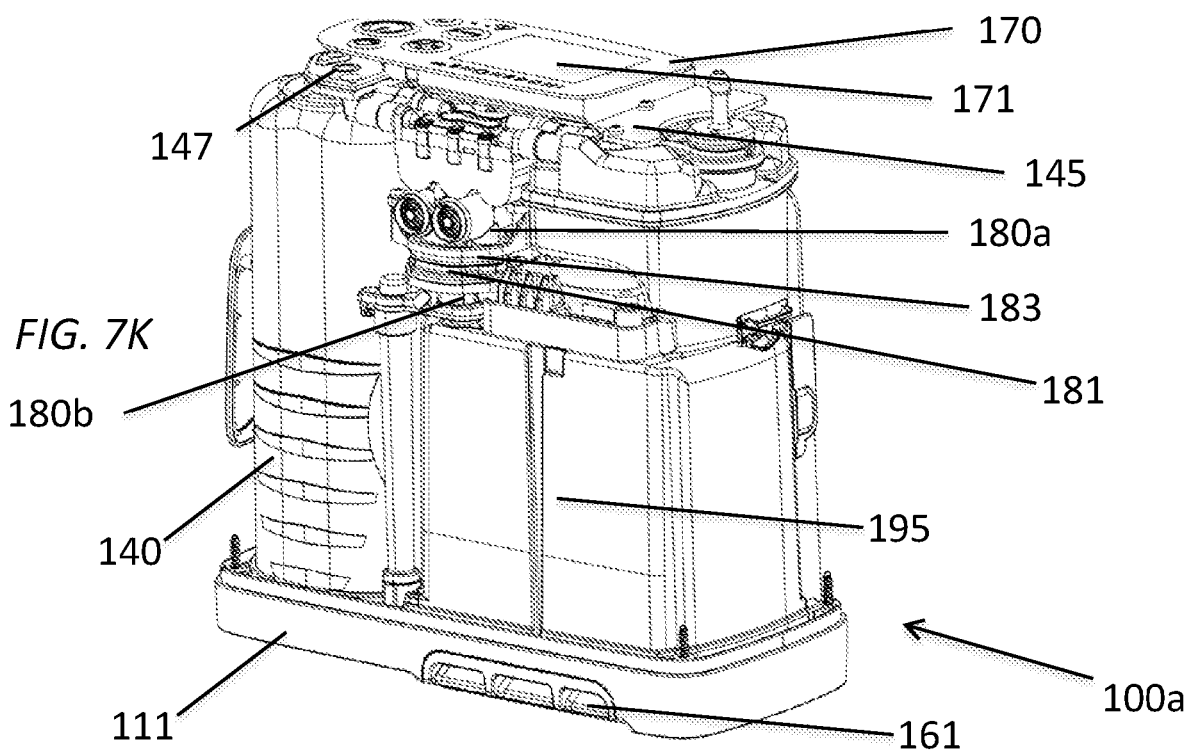

FIGS. 7J and 7K show interconnection assemblies have elements 181 and 183 mating with two sets of tubes—tubes 180a from a valve assembly and tubes 180b from a manifold assembly. When assembled together, the multi-port interconnect assembly having element 181 and 183 provides compact multiple gas connections in a small footprint, allows for elastomeric isolation between the two assemblies, and is easy to assemble.

As has been described in co-pending U.S. patent application Ser. Nos. 15/608,775 and 15/027,948, the mounting of a compressor or compressor assembly in a portable oxygen concentrator can requires the use of mate-able gas transport compliant members to accommodate the vibration levels of the compressors, as well as to dampen sound and vibration. In the case of mounts on the intake of the compressor, these members typically include circular tube connections and can be by necessity thin and flexible to maintain vibration isolation at low frequency rates of 150 Hz or below. Such connections are reliable and functional and may be fastened through the interior of the mount utilizing a screw or retainer with a hole through it for air intake into the compressor. However, during assembly, these round tube connections can allow for the connections to rotate due to the torque of the fastener, complicating the assembly process and introducing variability into the final assembled configuration. In the case of output of the compressor, compliant members may also twist or be incorrectly aligned during installation, also introducing assembly variation.

Figure 8A:
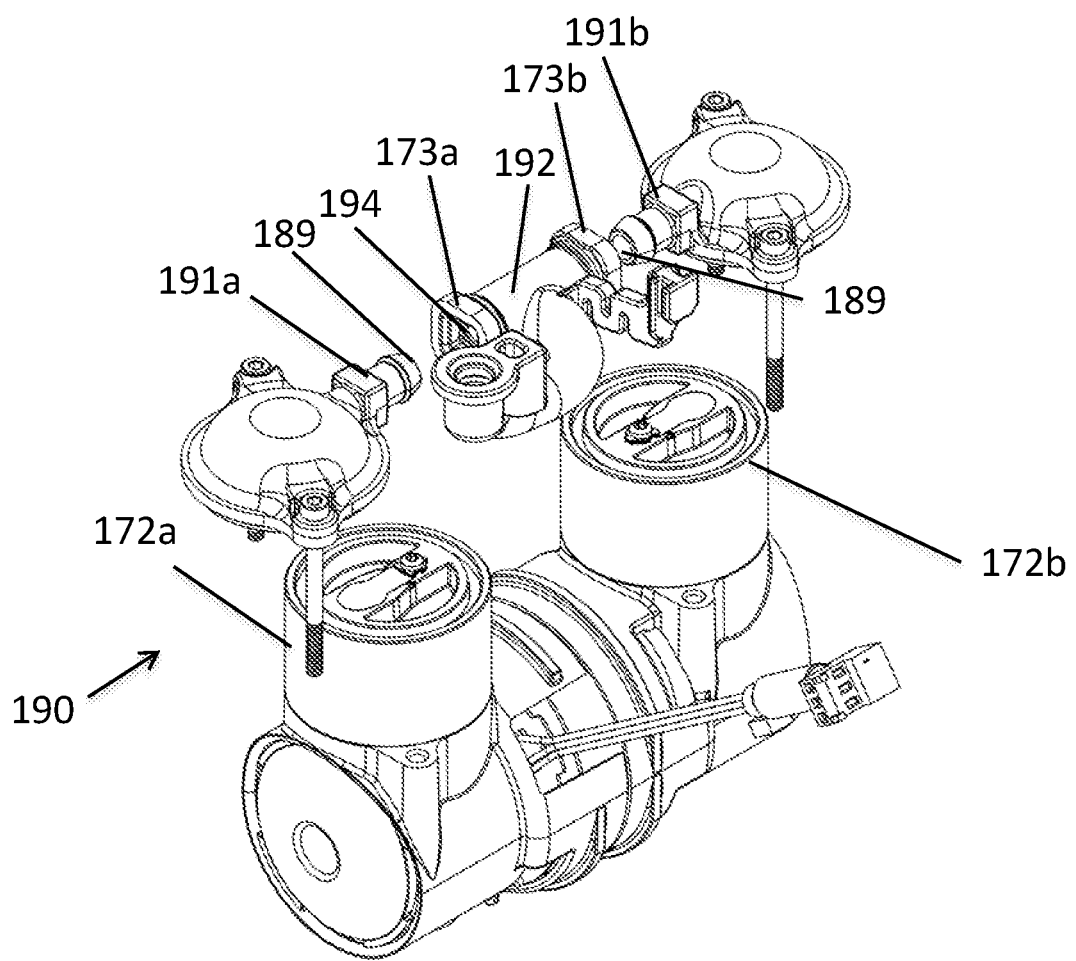
FIGS. 8A through 8D show various illustrative embodiments of compressor mounting elements of an exemplary portable oxygen concentrator.
Figure 8B:
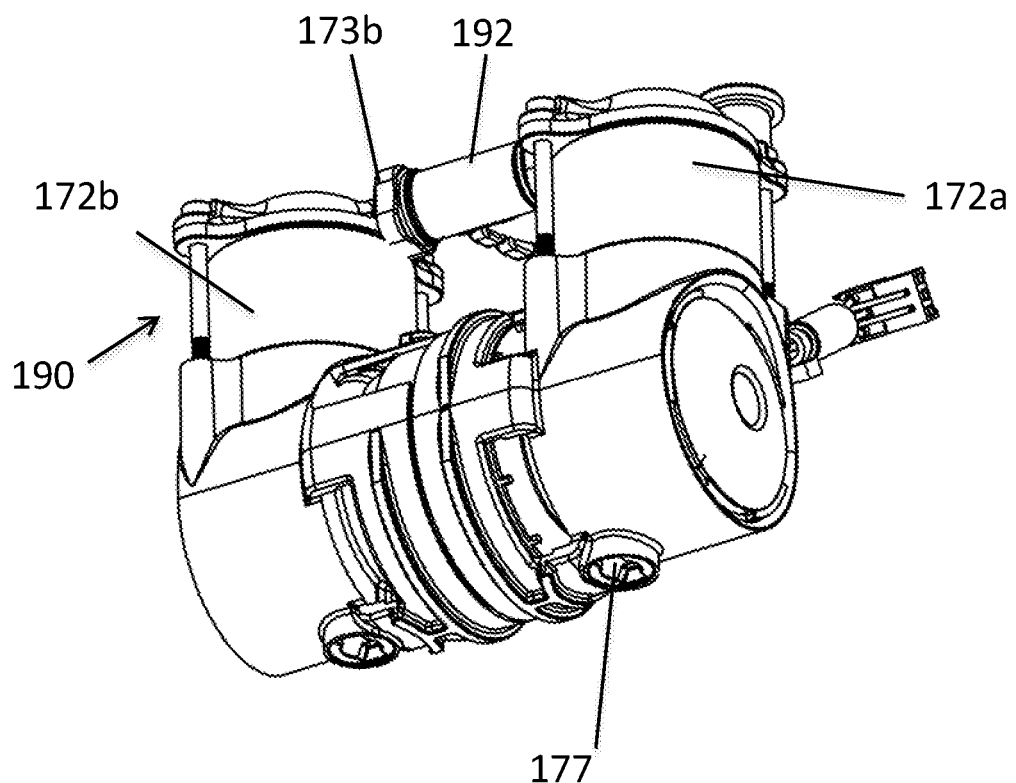
Figure 8C:
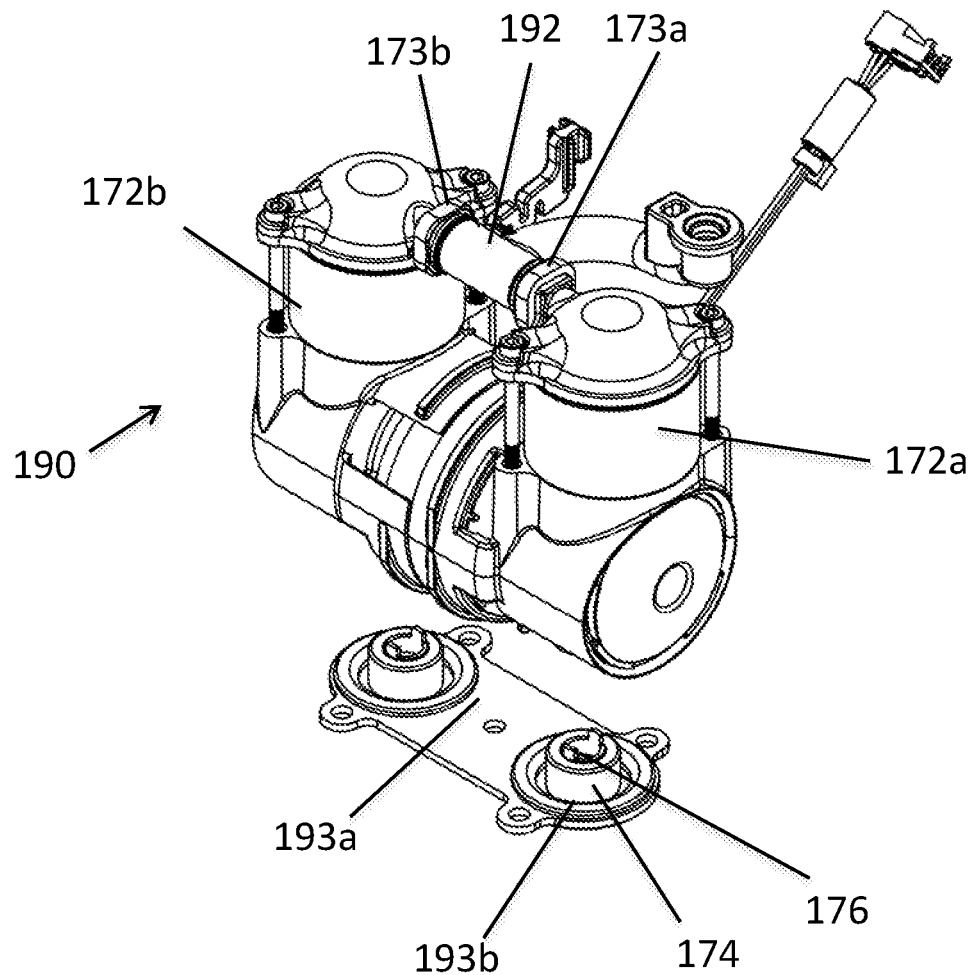
Figure 8D:
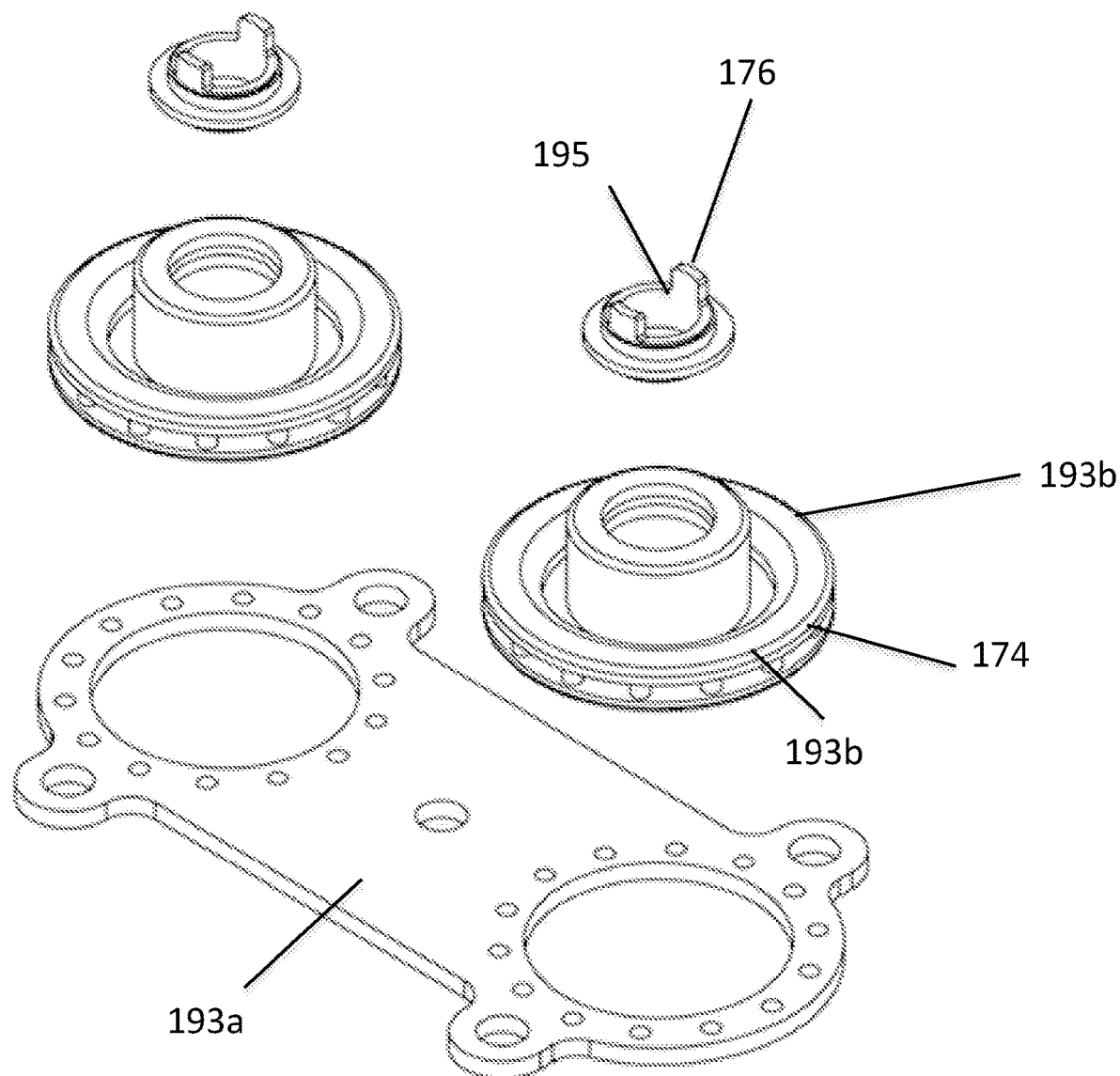

An improved arrangement is shown in FIGS. 8A-C. Compressor assembly 190 includes a first compressor chamber 172a having a first connector 191a and a second compressor chamber 172b having a connector 191b. The compressor assembly 190 further includes tube 192. The tube 192 includes a first end having a first connection interface 173a configured to couple to the first connector 191a to form a first interconnect. The compliant member 192 includes a second end having a second connection interface 173b configured to couple to the second connector 191b to form a second interconnect. A connection between the first connection interface 173a to the first connector 191a and the second connection interface 173b to the second connector 191b forms a gas connection between the first compressor chamber 172a and the second compressor chamber 172b.

In some embodiments, one or more of the first connector 191a, the second connector 191b, and the tube 192 can be compliant. Utilization of at least one compliant component can facilitate ease of connection between the tube 192 and both the first connector 191a and 191b.

The first connection interface 173a can be shaped, dimensioned, and/or otherwise configured to maintain the first interconnect in a fixed orientation. The second connection interface 173b can be shaped, dimensioned, and/or otherwise configured to maintain the second interconnect in a fixed orientation.

In some embodiments, the first connector 191a can have a shape that matches the shape of the first connection interface 173a. In some embodiments, the first connection interface 173a and the first connector 191a can be shaped such that the first connection interface 173a and the first connector 191a can mate in only one possible orientation. In some embodiments, the first connection interface 173a and the first connector 191a can be shaped such that the first connection interface 173a and the first connector 191a are prevented from rotating when mated. In some embodiments, the first connection interface 173a and the first connector 19a can be square, generally square, or any other suitable shape. In some embodiments, the second connector 191b can have a shape that matches the shape of the second connection interface 173b. In some embodiments, the second connection interface 173b and the second connector 191b can be shaped such that the second connection interface 173b and the second connector 191b can mate in only one possible orientation. In some embodiments, the second connection interface 173b and the second connector 191b can be shaped such that the second connection interface 173b and the second connector 191b are prevented from rotating when mated. In some embodiments, the second connection interface 173b and the second connector 191b can be square, generally square, or any other suitable shape.

In some embodiments, one or both of the first connector 191a and the second connector 191b can be in the form of protrusions. In some embodiments, one or both of the first connection interface 173a and the second connection interface 173b can be in the form of receptacles. Alternatively, in some embodiments, one or both of the first connector 191a and the second connector 191b can be in the form of receptacles, and one or both of the first connection interface 173a and the second connection interface 173b can be in the form of protrusions.

In some embodiments, a sealing element 189 can extend from each of the connectors 191a and 191b and into the tube 192 when the connectors 191a and 191b are coupled thereto. Each of the sealing elements 189 can be configured to form a seal with a complementary sealing element 194 positioned within an interior of the tube 192. Alternatively, in some embodiments, sealing elements 194 can extend from the tube 192 into the first connectors 191a and 191b to mate with complementary sealing elements 189 within the connectors 191a and 191b.

Mount 193 illustrates another type of clocking. The mount 193 includes a base 193a and one or more connectors 193b. Each of the connectors 193b can include a compliant member 174. Each of the connectors 193b can further include one or more protruding tabs 176 extending from the compliant member 174. In some embodiments, each of the connectors 193b can include a pair of protruding tabs 176. In some embodiments, the pair of protruding tabs 176 can be spaced 180 degrees apart from one another about a circumference of the compliant member 174. In some embodiments, the one or more protruding tabs 176 can be configured to couple with one or more complementary slots 177 on the compressor 190 configured to receive the pair of protruding tabs 176. In some embodiments, the coupling between the protruding tabs 176 and the slots 177 can clock the interconnect in a fixed orientation. Other tab/slot or post/hole arrangements may also be used. For example, in some embodiments, the mount 193 includes slots configured to receive protruding tabs from the compressor assembly 190.

In some embodiments, the protruding tabs 176 can be formed of a different material than the compliant member 174. In some embodiments, as shown in FIG. 8C, the protruding tabs 176 can be part of a separate clocking member or insert 195, which can be formed of a rigid material, such as metal or plastic. The insert 195 can adds rigidity to the clocking connection. In some embodiments, the compliant member 174 and the clocking member 195 may be attached during a molding process, joined with adhesives, or clamped together. In some embodiments, the base 193a may also be separately manufactured. In some embodiments, the base 193a can be formed of a rigid material such as metal or plastic. The base 193a can add rigidity to the clocking connection.

In some embodiments, the mount 193 can be coupled to the compressor assembly 190 by a hollow screw. In some embodiments, intake air can be drawn through the hollow screw.

In some embodiments, the inclusion of clocking arrangements for compliant member interconnects improves the manufacturing of the portable oxygen concentrator. In the absence of clocking members, compliant member 193 may twist during installation, which can lead to tearing of the material or the compressor assembly being held out of place by the twisting of the mount.

Portable oxygen concentrators can require compact $O_2$ sensors to monitor the oxygen content of the gas delivered to patients. Such sensors can be difficult to find commercially in the size range and price points required for portable oxygen concentrators. Accordingly, many commercial portable concentrators have custom designed oxygen sensors. These sensors generally rely on the fact that the speed of sound in a gas is dependent on the gas composition and therefore oxygen concentration can be inferred from the speed of sound.

Figure 9A:
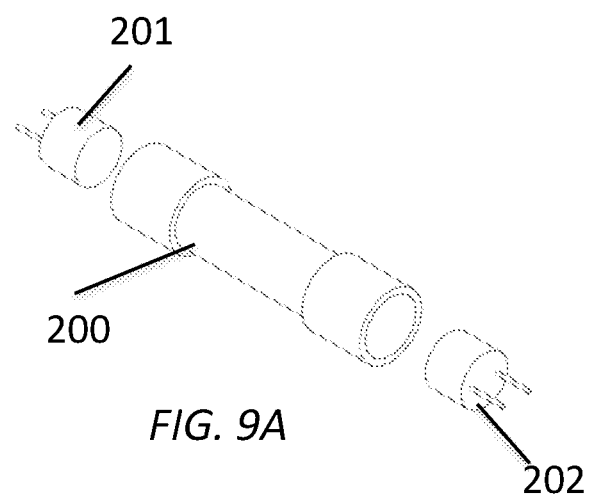
FIGS. 9A through 9F show various illustrative embodiments of elements of oxygen and other sensor block arrangements of an exemplary portable oxygen concentrator.
Figure 9B:
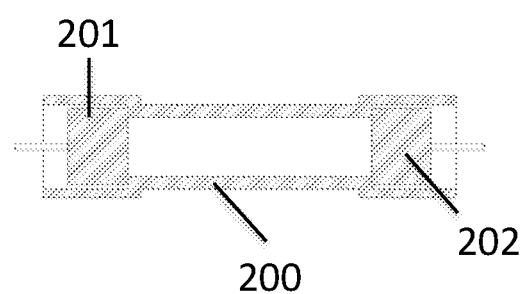

Examples of oxygen sensor designs for the oxygen concentrators are shown in FIGS. 9A and 9B. A sound emitter 201 is mounted to one end of tube 200, and a sound receiver 202 is mounted to the other end of the tube 100. In principle, a measurement can be performed based on the speed of sound (approximately 350 m/s), a length of the tube, and a transit time between the emitter 201 and the receiver 202. In practice, pressure and temperature variations affect signal reception rise time, and standing wave propagation may induce distortions that make the actual use of such a sensor problematic, and significant design and implementation issues affect this type of design. In addition, commercially available transducers are available in limited packaging options, potentially making the inclusion of such a sensor into the concentrator labor intensive.

Figure 9C:
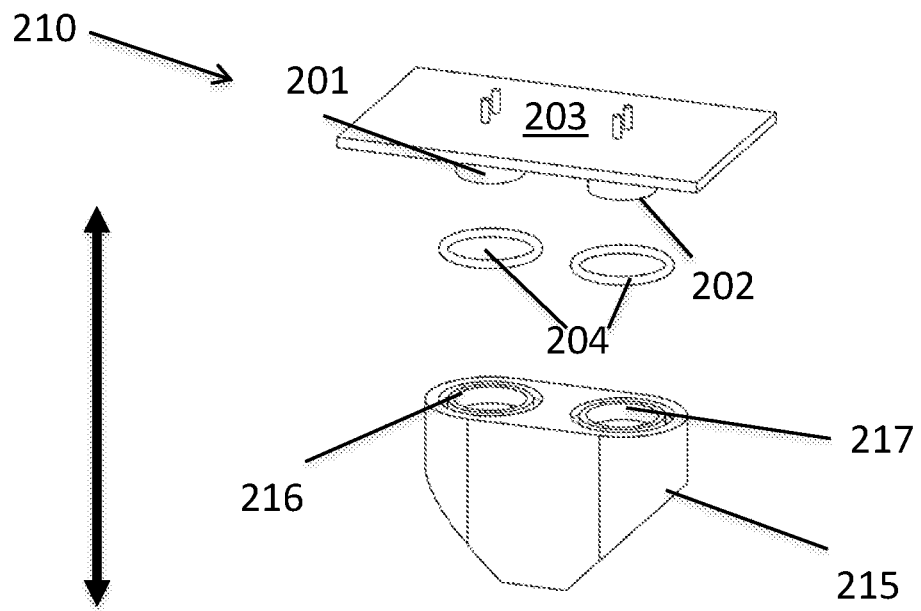
Figure 9D:
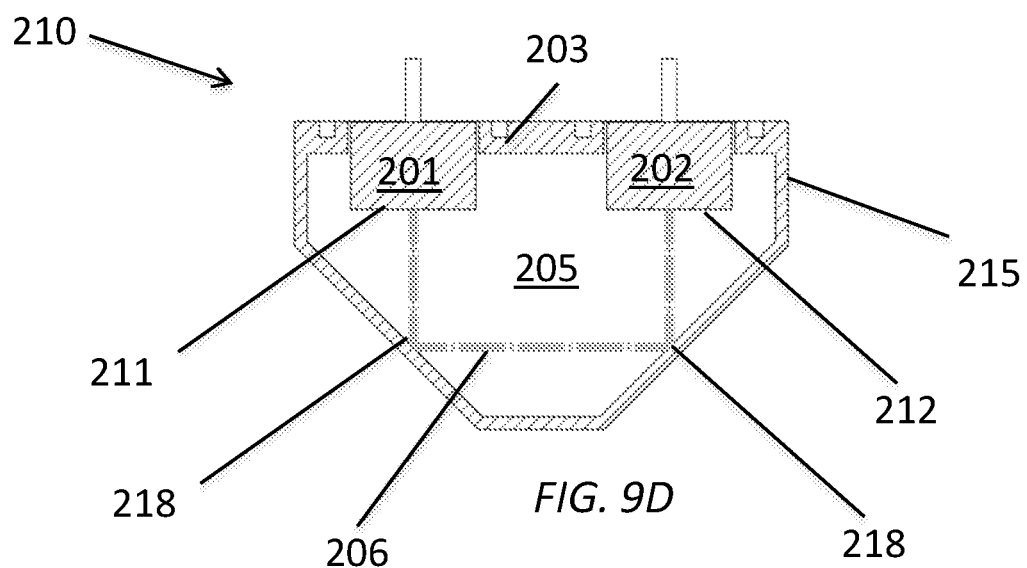

An alternative embodiment of an oxygen sensor 210 is shown in FIGS. 9C and 9D. The oxygen sensor 210 includes an emitter 201 comprising an active surface 211 configured to emit an acoustic signal. The oxygen sensor 210 includes a receiver 202 having an active surface 212 configured to receive an acoustic signal. The oxygen sensor 210 further includes a body 215 forming a chamber 205. The body 215 includes a first opening 216 configured to receive the emitter 201 such that the active surface 211 of the emitter 201 is exposed to the chamber 205. The body 215 includes a second opening 217 configured to receive the receiver 202 such that the active surface 212 of the receiver 202 is exposed to the chamber 205.

In some embodiments, body 215 can include one or more reflectors 218 configured to reflect an acoustic signal so as to establish an acoustic path between the active surface 211 of the emitter 201 and the active surface 212 of the receiver 202. In some embodiments, the body 215 can include at least two reflectors 218. In some embodiments, the reflectors 218 can be formed by or positioned on two angled opposing faces within the body 215. An example of an acoustic path 206 is shown in FIG. 9D. Alternative arrangements may include an acoustic path with one reflection or multiple reflections.

In some embodiments, the first opening 216 and the second opening 217 can be coplanar. In some embodiments, the first opening 216 and the second opening 217 can be positioned in parallel to one another. In some embodiments, the active surface 211 of the emitter 201 and the active surface 212 of the receiver 202 can be coplanar. In some embodiments, the emitter 201 and receiver 202 are mounted with their active surfaces 211 and 212 in the same orientation, for example, parallel with one another. In some embodiments, the active surface 211 of the emitter 201 and the active surface 212 of the receiver 202 are oriented to face in parallel directions.

In some embodiments, the oxygen sensor 210 further includes one or more seals 204. The seals 204 can be in the form of sealing rings. In some embodiments, the seals 204 can include a first seal 204 configured to provide a seal between the first opening 216 and the emitter 201 and a second seal 204 configured to provide a seal between the second opening 217 and the receiver 202.

Figure 9E:
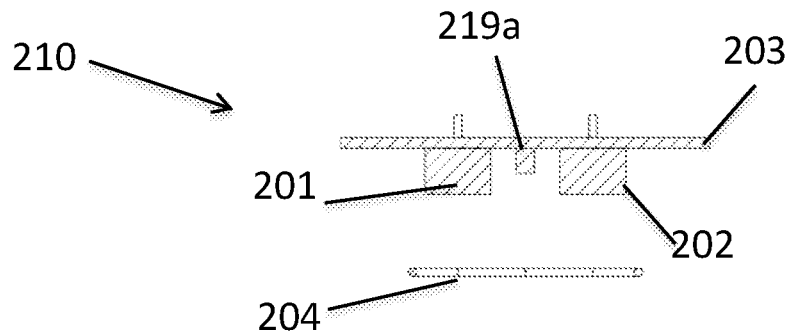
Figure 9F:
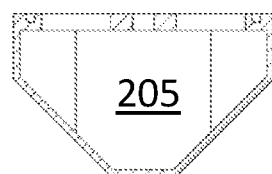
Figure 9F:
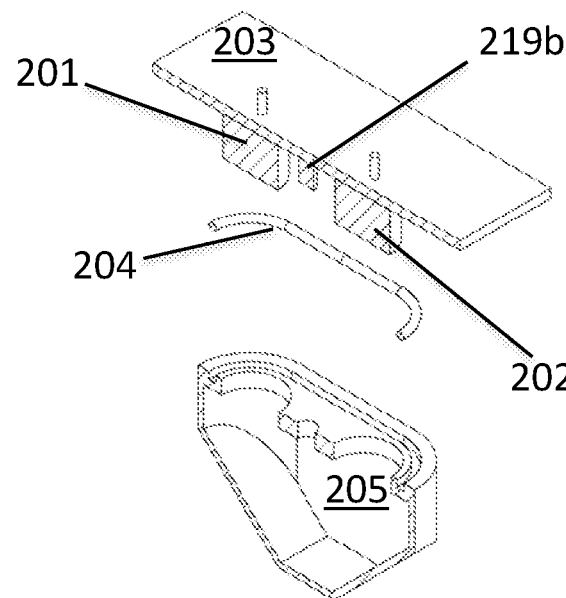

In some embodiments, the sensor 210 can include a printed circuit board 203. In some embodiments, the emitter 201 and receiver 202 can be co-mounted to the printed circuit board 203. In some embodiments, one or more additional sensors, such as a temperature sensor 219a and/or a pressure sensor 219b as shown in FIGS. 9D, 9E, and 9F, may be co-mounted to the PCB 203. In some embodiments, the body 215 may mount directly to the PCB 203. In some embodiments the body 215 and seals 204 can mount directly to the PCB.

In some embodiments, the temperature sensor 219a can be configured to measure a temperature of oxygen gas within the chamber 205. In some embodiments, the temperature sensor 219a can be configured to measure a temperature of air outside the chamber 205.

In some embodiments, the pressure sensor 219b can be configured to measure a pressure of oxygen gas within the chamber 205. In some embodiments, the pressure sensor 219b can be configured to measure the pressure of air outside the chamber 205.

In some embodiments, the sound path 206 within the chamber 205 may be configured to reduce standing wave propagation, eliminating or at least reducing one of the difficult to characterize behaviors of the tube type sensors shown in FIGS. 9A-B.

Many portable oxygen concentrators provide two or more output flow settings, thereby allowing a single model concentrator to address a range of patient oxygen needs. In some embodiments, it may be desirable for the compressor for such concentrators to be designed with a maximum flow setting driving the intended compressor capacity. However, it is often the case that most users will operate a given concentrator model at a flow setting lower than maximum flow during use of the oxygen concentrator. In some instances, a user will operate the oxygen concentrator at a number of different settings during use. In some instances, a user will operate the oxygen concentrator at a setting lower than the maximum flow setting during a majority of the duration of use of the concentrator. Thus, even though a compressor motor must be capable of operating at the maximum flow setting, the highest flow setting may not be used often. Accordingly, it may be advantageous to tune the motor and motor control function to improve efficiency at the most commonly used flow settings while maintaining the ability to operate across the full range of flow settings.

Figure 10A:
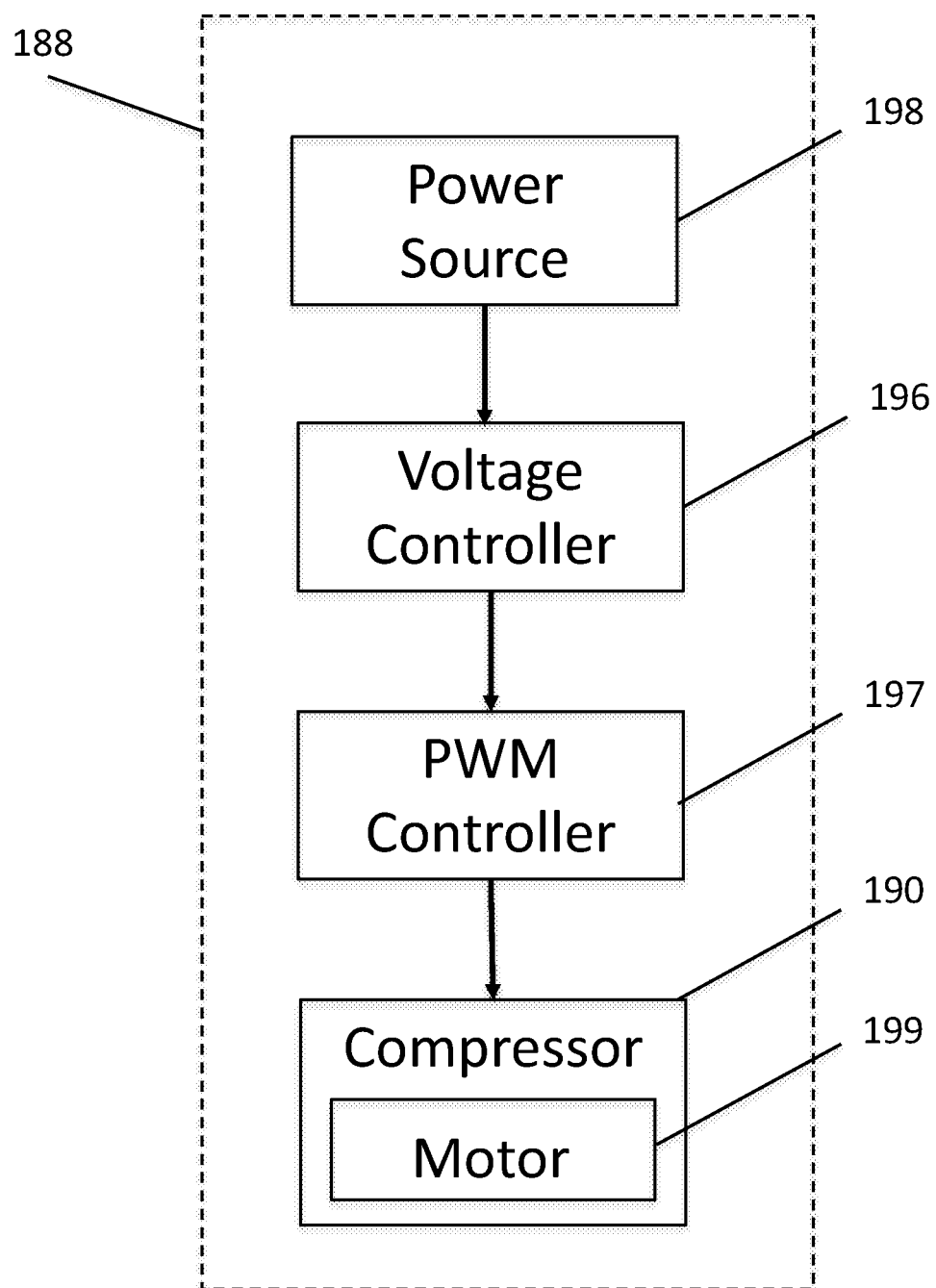
FIGS. 10A through 10F show various illustrative elements of compressor motor control of an exemplary portable oxygen concentrator.

Referring to FIG. 10A, a simplified illustration of a control system 188 for controlling a motor 199 of the compressor 190 is shown. The control system 188 includes a power source 198, a voltage controller 196, and a pulse width modulation (PWM) controller 197. In some embodiments, the voltage controller 196 and PWM controller 197 can be combined into a single motor controller or, alternatively, may be separate elements.

In some embodiments, the power source 198 provides a power source voltage. In some embodiments, the power source 188 provides a DC power source voltage. In some embodiments, the power source is a battery, an AC to DC power supply, a fixed power source having car DC power ports, or any other suitable power source.

In some embodiments, one or both of the voltage controller 196 and the PWM controller 197 can drive operation of the compressor 190, for example, by providing compressor motor control signals. In some embodiments, the voltage controller 196 is configured to selectively modify the power source voltage to provide a plurality of supply voltages. In some embodiments, the voltage controller 196 is configured to modify the power source voltage to provide one or more supply voltages higher than the power source voltage.

In some embodiments, the pulse width modulation controller 197 is configured to selectively apply pulse width modulation to supply voltages at plurality of pulse width modulation duty cycles. In some embodiments, one or both of the voltage controller 196 and PWM controller 197 can be used to provide a plurality of motor control signals to the motor 199.

In some embodiments, for example, when the power source 188 is a battery, the method for operating the compressor 190 further includes dynamically monitoring the power source voltage and adjusting one or both of the supply voltage and the pulse width modulation duty cycle to accommodate power source voltage changes to achieve a desired efficiency of the compressor.

Figure 10B:
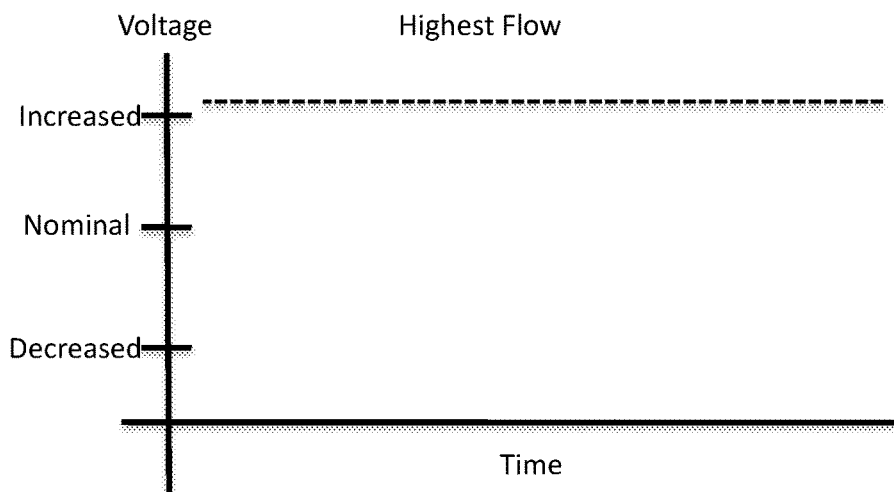
Figure 10C:
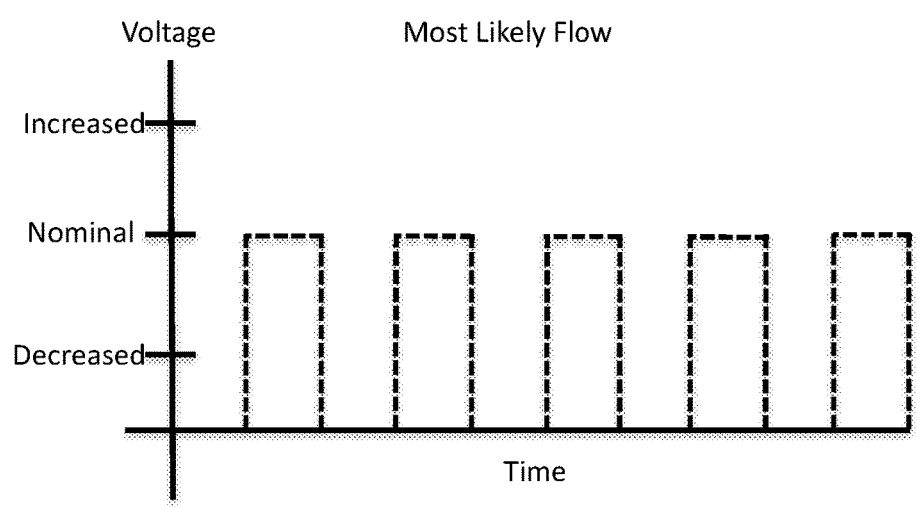

FIGS. 10B-C show examples of oxygen concentrator voltages over time. Many oxygen concentrators operate in a manner illustrated in FIG. 10C. A nominal voltage is supplied from a power source, and the motor speed and therefore compressor output is controlled by applying PWM control to the nominal voltage, varying the motor speed by changing the duty cycle of the PWM supply signal. Thus, a low duty cycle is applied for the lowest settings varying up to a very high duty cycle or even a non-modulated DC signal for the highest settings.

However, the voltage level of the nominal voltage also has an effect of compressor efficiency. For example, switching losses when PWM is applied may be lower if the voltage level is lower. Losses may be minimized by modulating the nominal voltage, for example, using a voltage controller 196, and keeping the PWM duty cycle near 100%, or, alternatively at or near a certain target threshold. Additionally, the efficiency curve of a given compressor motor can roll off at higher torques at a given speed for a certain supply voltage. In general, the efficiency of a compressor motor and controller operation has been found to be a function of both PWM duty cycle and voltage supply level. It is possible to measure, e.g. calibrate, motor efficiency over a range of supply voltage/PWM duty cycle combinations to optimize battery lifetime for each combination.

Battery lifetime naturally varies significantly with concentrator output flow. For one concentrator design produced by the applicant of the current disclosure, with six settings, the most common setting used by patients is the second from the lowest setting. At this setting, the concentrator may have several hours of battery life, for example 10 hours. At the highest flow setting, the concentrator may have one hour of use time. Therefore, an adjustment of efficiency that say adds 10% to the most used setting will add a full hour of use time. If the improvement in efficiency at the most common setting results in a 10% loss at the high setting, that penalty is only six minutes. It is therefore advantageous to tune the compressor motor control to achieve higher efficiency at the commonly used lower settings, and this tuning can be improved by varying the supply voltage as well as the PWM duty cycle, for example, by the voltage controller 196 and PWM controller 197 as described above.

Accordingly, a method of operating an oxygen concentrator can include modifying the power source voltage using the voltage controller 196 and the PWM controller 197. A concentrator design can be calibrated over a range of supply voltages and PWM duty cycles, possibly with the maximum setting representing a very high duty cycle and/or the highest achievable voltage.

Figure 10D:
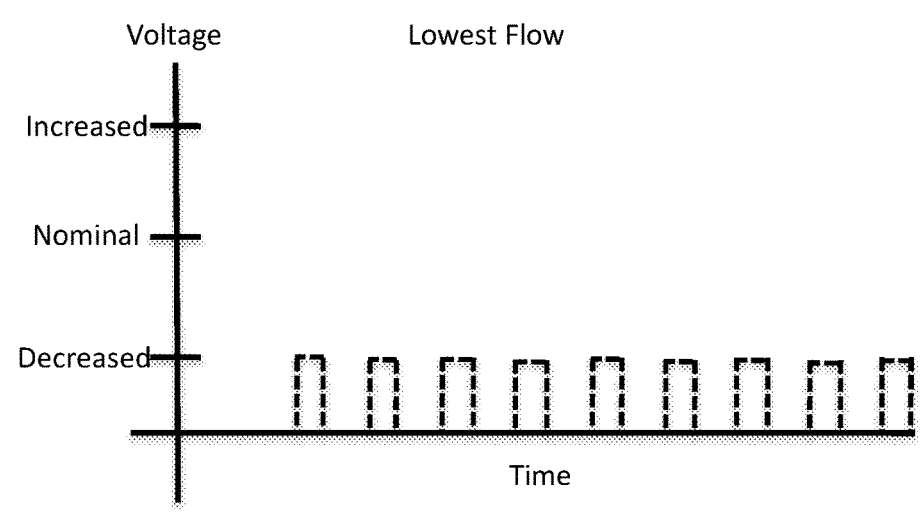
Figure 10E:
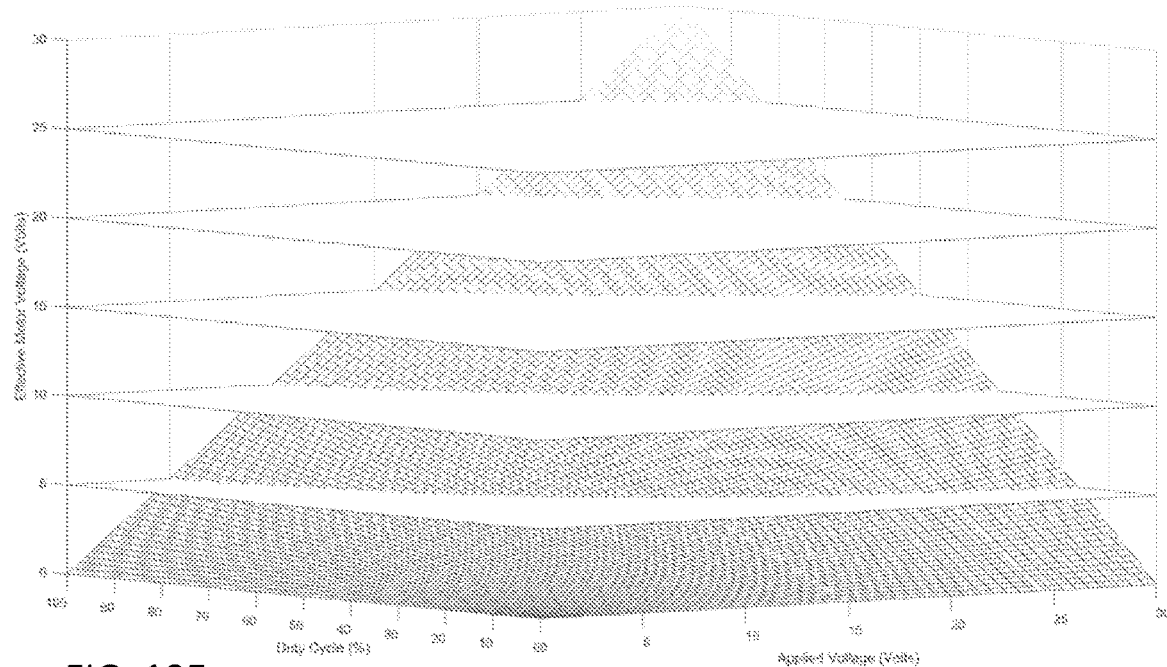
Figure 10F:
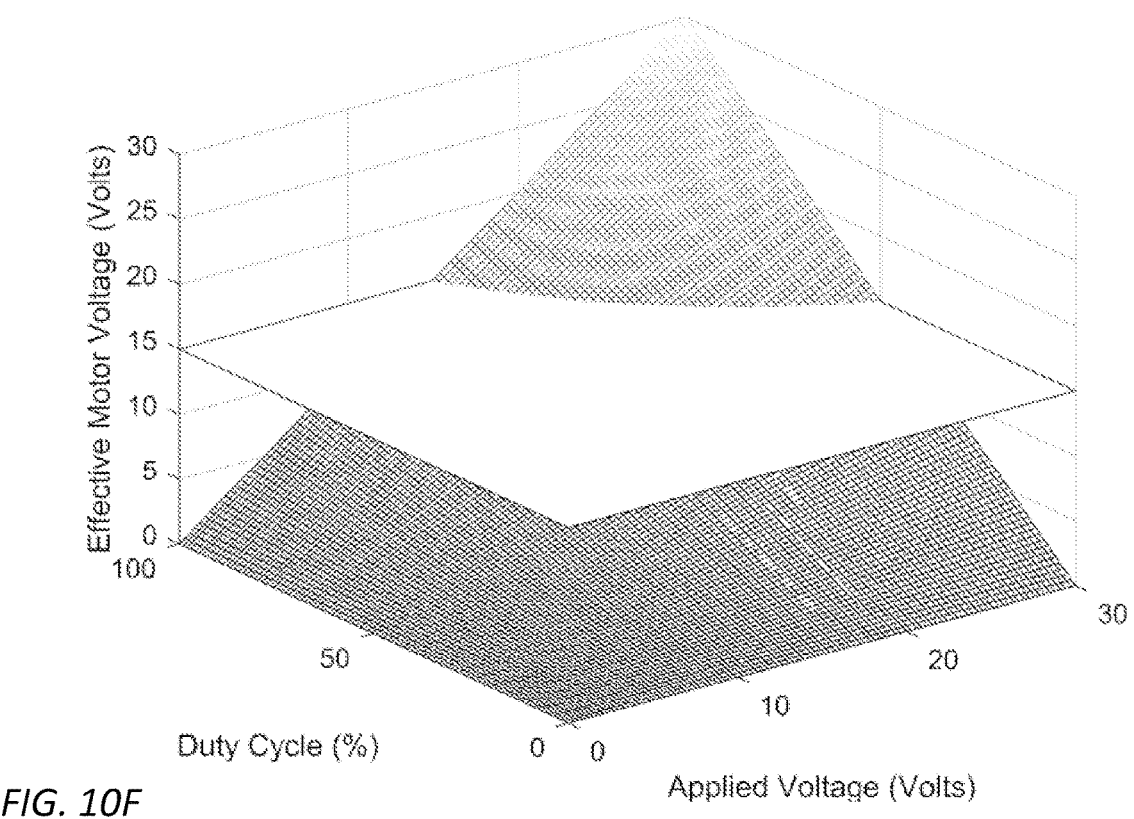

For some concentrator designs, efficiencies as a function of supply voltage/PWM duty cycle may be calculated, modeled, or measured. Some combination of techniques may be used. In some embodiments, a nominal voltage may be supplied which may be increased or decreased concurrently, for example, by the voltage controller 196, with PWM control, for example, by the PWM controller 197, to achieve efficiency targets at each flow setting. The use of a supply voltage controller 196 in addition to the PWM controller 197 may result in a decreased compressor-motor-controller efficiency at certain operational points due to the operation of these electronics, but an optimum configuration can be found that results in minimal losses at a desired design point. These losses may then be less than losses encountered from a PWM only control based system, resulting in a higher overall system efficiency. For example, in some embodiments, switching losses may be reduced. In FIGS. 10B-D, a nominal voltage and a PWM rate that is selected from calibration data that achieves desirable efficiency at a most common setting is supplied. FIGS. 10C and 10D show similar amounts of effective voltage being applied to the motor for different amounts of applied voltage and PWM duty cycle applied. For the less common settings, a combination of increasing or decreasing supply voltage and changing PWM duty cycle is applied. Of course, other combinations may be used as well, such as providing a DC voltage configured for the highest setting, and lowering the voltage and changing PWM for each lower setting. However, when the nominal settings are picked, the result is that both supply voltage and PWM duty cycle are varied to selectively increase efficiency at desired flow settings. This can be illustrated in the surface plot in FIGS. 10E and 10F, which show how the effective motor voltage is a function of a combination of both applied voltage and the PWM duty cycle. The intersection of a given horizontal plane with the surface plot exemplifies the available combination of PWM and applied voltage that results in the same effective motor voltage along the intersecting line. Along this line is a maximum efficiency point that can be measured or calculated.

Battery-operated devices can have various supply voltages, such as from a car or an AC to DC power supply, as well as various voltages depending upon the state of charge or depletion of the battery. It is possible to monitor the dynamically changing battery voltage and accordingly modify the PWM duty cycle and voltage to the controller dynamically to maximize system efficiency. It is also possible to increase the supply voltage relative to battery voltage on some higher flow settings to achieve desired motor performance while letting the voltage available from the battery to pass through and utilize only PWM control on other flow settings.

In some embodiments, a method for operating a compressor assembly 190 includes determining an efficiency of the compressor assembly 190. Determining the efficiency of the compressor assembly 190 can include measuring, calibrating, calculating, or modeling motor efficiency of the motor 199 over a range of supply voltage and pulse width modulation duty cycle combinations. Each combination can include a supply voltage from the voltage controller 196 and a pulse width modulation duty cycle from the pulse width modulation controller 197.

In some embodiments, the method for operating the compressor assembly 190 can include selecting a supply voltage and a pulse width modulation duty cycle for use at at least one output flow setting based on the determined efficiency of the compressor assembly 190.

In some embodiments, the method for operating the compressor 190 assembly 190 can include generating the selected supply voltage by maintaining, reducing, or increasing a nominal supply voltage, for example, using the voltage controller 196. In some embodiments, the nominal supply voltage is a desired voltage for one of the plurality of output flow settings. In some embodiments, the nominal supply voltage is a desired supply voltage for a maximum output flow setting. In some embodiments, the nominal supply voltage is used without pulse width modulation as the motor control signal for a highest output flow setting of the plurality of outflow settings of the compressor assembly 190. In some embodiments, a combination of supply voltage regulation, for example, using the voltage controller 196, and pulse width modulation, for example, using the PWM controller 197, are applied to the nominal supply voltage to provide motor control signals to the motor 199 for one or more output flow settings lower than the highest output flow setting of the compressor assembly 190.

In some embodiments, the selected supply voltage and the selected pulse width modulation duty cycle are selected to optimize efficiency at a most commonly used output flow setting of the plurality of output flow settings while maintaining the ability to operate at each of the plurality of output flow settings.

In some embodiments, the selected supply voltage and the selected pulse width modulation duty cycle are selected to reduce switching losses at at least one output flow setting of the plurality of output flow settings.

In some embodiments, the method for operating the compressor 190 can include applying the selected pulse width modulating duty cycle.

In addition to having multiple flow settings, the nature of a swing adsorption system results in a head profile that changes dynamically over the course of a pressure, pressure-vacuum, or vacuum swing cycle. The amount that the load on the compressor motor and control electronics varies over the course of a cycle depends on the number of valves utilized, number of beds used, product gas tank used, and sequencing and timing (e.g. specific PSA cycle employed) and can thus vary from ~0-30 psi. It is therefore advantageous to modulate the controller voltage and PWM duty cycle dynamically to optimize efficiency over the course of a PSA cycle. This can be performed in real-time using current, power, or pressure measurements, a feed-forward method using any of the aforementioned, any combination of them, or other techniques.

In some embodiments, in which the compressor is part of a swing adsorption system, the method for operating the compressor 190 can include monitoring a pressure profile over the course of a pressure swing adsorption cycle, a pressure-vacuum swing adsorption cycle, or a vacuum swing adsorption cycle. In some embodiments, the method can include dynamically adjusting the supply voltage and pulse width modulation duty cycle to improve efficiency over the course of the pressure swing adsorption cycle, the pressure-vacuum swing adsorption cycle, or the vacuum swing adsorption cycle. In some embodiments, monitoring the head profile and adjusting the supply voltage and pulse width modulation duty cycle are performed during the pressure swing adsorption cycle, the pressure-vacuum swing adsorption cycle, or the vacuum swing adsorption cycle. In some embodiments, monitoring the head profile includes monitoring one or more of current measurements, power measurements, and pressure measurements through a feed forward process.

The embodiments described herein are exemplary. Modifications, rearrangements, substitute processes, alternative elements, etc. may be made to these embodiments and still be encompassed within the teachings set forth herein. One or more of the processes described herein may be carried out by one or more processing and/or digital devices, suitably programmed.

The various illustrative processing, data display, and user interfaces described in connection with the embodiments disclosed herein can be implemented as electronic hardware, computer software, or combinations of both. To clearly illustrate this interchangeability of hardware and software, various illustrative components, blocks, and modules have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A gas concentrator, comprising:
   a chassis base;
   a compressor assembly;
   an airflow generator;
   a plurality of exhaust ports, wherein the plurality of exhaust ports comprises a first exhaust port and a second exhaust port, wherein the first exhaust port and the second exhaust port are formed within opposite side surfaces of the chassis base; and
   an outer housing coupled to the chassis base so as to define an internal volume enclosing the compressor assembly and the airflow generator, the outer housing comprising one or more air inlets, wherein the one or more air inlets are recessed within the outer housing or extend along a curved or angled surface of the outer housing;
   wherein the airflow generator is configured to direct airflow along an airflow path between the one or more air inlets and the plurality of exhaust ports.

2. The gas concentrator of claim 1, wherein the one or more air inlets comprise a first air inlet and a second air inlet, wherein the first air inlet and the second air inlet are positioned on opposite surfaces of the housing.

3. The gas concentrator of claim 1, wherein the one or more air inlets are recessed within the outer housing.

4. The gas concentrator of claim 1, wherein the one or more air inlets extend along the curved or angled surface of the outer housing.

5. The gas concentrator of claim 1, further comprising a shell structure comprising one or more insulating panels disposed about the compressor assembly.

6. The gas concentrator of claim 5, wherein the shell structure is configured to separate cooling airflow from spent airflow having a higher temperature than the cooling airflow.

7. The gas concentrator of claim 1, wherein each of the exhaust ports comprises a recessed opening extending at least partially into a sidewall of the chassis base and at least partially into a lower surface of the chassis base.

8. The gas concentrator of claim 1, wherein each of the exhaust ports comprises an opening configured to provide at least two airflow paths from the gas concentrator, wherein the at least two airflow paths comprise a first airflow path and a second airflow path offset from the first airflow path.

9. The gas concentrator of claim 8, wherein the first airflow path is perpendicular to the second airflow path.

10. A gas concentrator, comprising:
    a chassis base;
    a compressor assembly;
    an airflow generator;
    one or more exhaust ports;
    an outer housing coupled to the chassis base so as to define an internal volume enclosing the compressor assembly and the airflow generator, the outer housing comprising one or more air inlets, wherein the one or more air inlets are recessed within the outer housing or extend along a curved or angled surface of the outer housing; and
    a battery coupled to the chassis base, wherein the one or more exhaust ports are formed in a portion of the chassis base extending laterally beyond a lateral edge of the battery;
    wherein the airflow generator is configured to direct airflow along an airflow path between the one or more air inlets and the one or more exhaust ports.

11. The gas concentrator of claim 10, wherein the one or more exhaust ports are directed at a downward angle over a recess formed in the portion of the chassis base extending laterally beyond the lateral edge of the battery, thereby preventing obstruction of the one or more exhaust ports if the concentrator is placed adjacent a flat surface.

12. The gas concentrator of claim 10, wherein the one or more air inlets comprise a first air inlet and a second air inlet, wherein the first air inlet and the second air inlet are positioned on opposite surfaces of the housing.

13. The gas concentrator of claim 10, wherein the one or more exhaust ports comprise a first exhaust port and a second exhaust port, wherein the first exhaust port and the second exhaust port are formed within opposite side surfaces of the chassis base.

14. The gas concentrator of claim 10, wherein the one or more air inlets are recessed within the outer housing.

15. The gas concentrator of claim 10, wherein the one or more air inlets extend along the curved or angled surface of the outer housing.

16. The gas concentrator of claim 10, further comprising a shell structure comprising one or more insulating panels disposed about the compressor assembly.

17. The gas concentrator of claim 16, wherein the shell structure is configured to separate cooling airflow from spent airflow having a higher temperature than the cooling airflow.

18. The gas concentrator of claim 10, wherein each of the one or more exhaust ports comprises a recessed opening extending at least partially into a sidewall of the chassis base and at least partially into a lower surface of the chassis base.

19. The gas concentrator of claim 10, wherein each of the one or more exhaust ports comprises an opening configured to provide at least two airflow paths from the gas concentrator, wherein the at least two airflow paths comprise a first airflow path and a second airflow path offset from the first airflow path.

20. The gas concentrator of claim 19, wherein the first airflow path is perpendicular to the second airflow path.

* * * * *